(12) United States Patent
Kim et al.

(10) Patent No.: US 6,670,130 B1
(45) Date of Patent: Dec. 30, 2003

(54) OLIGONUCLEOTIDE FOR DETECTION AND IDENTIFICATION OF MYCOBACTERIA

(75) Inventors: Cheol Min Kim, Pusan Metropolitan (KR); Hee Kyung Park, Seoul (KR); Hyun Jung Jang, Pusan Metropolitan (KR)

(73) Assignee: SJ Hightech Co., Ltd. (KR)

( * ) Notice: Subject to any disclaimer, the term of this patent is extended or adjusted under 35 U.S.C. 154(b) by 0 days.

(21) Appl. No.: 09/980,052

(22) PCT Filed: May 16, 2000

(86) PCT No.: PCT/KR00/00477

§ 371 (c)(1),
(2), (4) Date: Nov. 28, 2001

(87) PCT Pub. No.: WO00/73436

PCT Pub. Date: Dec. 7, 2000

(30) Foreign Application Priority Data

| May 29, 1999 | (KR) | F1999-19631 |
| May 29, 1999 | (KR) | 1999/19632 |
| May 29, 1999 | (KR) | 1999/19633 |
| May 29, 1999 | (KR) | 1999/19634 |
| Apr. 7, 2000 | (KR) | 2000/181189 |

(51) Int. Cl.[7] ............. C12Q 1/68; C12P 19/34; C07H 21/02; C07H 21/04

(52) U.S. Cl. ............. 435/6; 435/7.2; 435/91.1; 435/91.2; 536/23.1; 536/23.7; 536/24.1; 536/24.3; 536/24.32; 536/24.33

(58) Field of Search ............. 435/6, 7.2, 91.1, 435/91.2; 536/23.1, 23.7, 24.1, 24.3, 24.32, 24.33

(56) References Cited

U.S. PATENT DOCUMENTS 6,235,484 B1 * 5/2001 Hogan et al. ............. 435/6

OTHER PUBLICATIONS

Stackebrandt E., et al., "The primaty structure of the 16SrRNA of *Mycobacterium leprae*: its use in phylogeny and development of DNA probes", vol. 7. Suppl. 1, Acta Leprol. 1989 p. 222–225.

Roth A., et al., "Differentiation of phylogenetically related slowly growing mycobacteria based on 16S–23S rRNA gene internal transcribed spacer sequences", vol. 36. No. 1, J. of Clin. Microbiology 1998, pp. 139–147.

Cox RA, et al., "The 16S ribosomal RNA of *Mycobacterium leprae* contains a unique sequence which can be used for identification by the polymerase chain reaction", vol. 35. No. 5, J of Clin.

Volker Gurtler, et al., "New approaches to typing and indentification of bacteria using the 16S–23S rDNA spacer region", Microbiology (1996), 142, pp. 3–16.

Jeanett Bauer, et al., "Usefulness of Spoligotyping to discriminate IS6110 low–copy–number *Mycobacterium tuberculosis* complex strains cultured in Denmark", Journal of Clinical Microbiology, Aug. 1999, pp. 2602–2606.

A. Troesch, et al., "Mycobacterium species identification and rifampin resistance testing with high–density DNA probe arrays", Journal of Clinical Microbiology, Jan. 1999, pp. 49–55.

William R. Jacobs, Jr. et al., "Rapid assessment of drug susceptibilities of mycobacterium tuberculosis by means of luciferase reporter phages", Science, vol. 260, May 7, 1993, pp. 819–821.

* cited by examiner

Primary Examiner—Kenneth R. Horlick
(74) Attorney, Agent, or Firm—Cantor Colburn LLP

(57) ABSTRACT

This invention relates to oligonucleotides sequence of probes or primers for detection or identication of Mycobacterium. In the claimed invention, oligonucleotide sequences of ITS (Internal Transcribing Spacer Region) from *M. fortuitium*, *M. chelonae*, *M. abscessus*, *M. vaccae*, *M. flavescence*, *M. Asiaticum*, *M. porcinum*, *M. acapulcensis* and *M. diernhoferi* have been identified. Using these ITS sequences, PCR primers or hybridization probes for detection or identication of Mycobacterium have been developed and presented as seq ID: 10 to seq ID: 241.

3 Claims, 4 Drawing Sheets

OLIGONUCLEOTIDE FOR DETECTION AND IDENTIFICATION OF MYCOBACTERIA

BACKGROUND OF THE INVENTION

1. Field of the Invention

The present invention relates to oligonucleotides that can be used for detection and identification of mycobacteria. More particularly, the present invention identifies the nucleotide sequence of ITS (Internal Transcribed Spacer region) of non-tuberculosis mycobacteria, *Mycobacterium fortuitum, Mycobacterium chelonae, Mycobacterium abscessus, Mycobacterium vaccae, Mycobacterium flavescens, Mycobacterium asiaticum, Mycobacterium porcinum, Mycobacterium acapulcensis* and *Mycobacterium diernhoferi*, and using the nucleotide sequences, it provides oligonucleotide primers or probes used for detection and identification of mycobacteria.

2. Description of the Related Art

A Even though the number of patients of tuberculosis has steadily decreased in these days, about 8 million patients have come out and about 3 million patients died of tuberculosis in a year. Moreover, in underdeveloped countries, inadequate treatment and lack of drugs for tuberculosis increase chronic carriers of drug-resistant bacteria. In 1980's, spread of AIDS has increased patients of tuberculosis even in advanced countries. In this condition, it is expected that about twelve million patents of tuberculosis would newly come out in the year 2000 (J. P. Natain, M. C. Raviglione, and A. Kochi, *Tubercle and Lung Disease*, 73: 311–321, 1992; Murray C J L. And Lopez A D. The global burden of disease. *Global burden of disease and injury series.* Vol. 1. Cambridge, Mass.: Harvard University Press, 1996, p349–350; Global Tuberculosis Programme: Anti-tuberculosis drug resistance, WHO Report 1997: World Health Organization. 1997).

In 1950's, it was reported that non-tuberculosis mycobacteria (NTM) has been able to cause diseases in human. After the report that *M. avium* complex (MAC) would bring about systemic disease in the patients of AIDS in 1980, non-tuberculosis mycobacteria have taken an interest. Diseases caused by non-tuberculosis mycobacteria are similar to tuberculosis in clinical condition and general pathological view. Non-tuberculosis mycobacteria are distributed in a wide range of living environment, and it is difficult to judge whether they have pathogenicity or not in clinical test sample. Further, since they have resistance to a number of drugs for tuberculosis, the infection is hard to treat and the recurrence rate is high. The infection of non-tuberculosis mycobacteria should be treated by other means than for tuberculosis, and therefore, accurate and fast method of detecting and identifying non-tuberculosis mycobacteria is required. The accurate and fast method of detecting and identifying both TB complex and NTM is also needed for effective treatment and management of tuberculosis.

Many a method has been developed to diagnose mycobacterial infection and to detect and identify mycobacteria strains. Among them, the following methods are used at present;

The first is a microbiological method, that is, smearing, staining and culturing test. However, this method is not suitable for mycobacteria, since they have long generation term and need long culturing time. Further, such pathogenic microorganism as mycobacteria is dangerous to infect the personnel in culture room;

The second is a PCR (Polymerase Chain Reaction) method. It is highly sensitive and specific to the mycobacteria and very useful to detect mycobacteria which have a long culturing time. Especially, it does not require a culturing process but uses a small amount of DNA to be amplified, therefore, only a small amount of pathogens in test sample is enough to detect and identify mycobacteria. Many a PCR process has been introduced with different target DNAs each other, and IS6110 and 16S rRNA are often used as the target (Bauer J, Andersen A B, Kremer K, and Miorner H, Usefulness of spoligotyping to discriminate IS6110 low-copy-number *Mycobacterium tuberculosis* complex strains cultured in Denmark, 1999, *J. Clin. Microbiol.* 37: 2602–2606; Troesch, A., H. Nguyen, C. G. Miyada, S. Desvarenne, T. R. Gingeras, P. M. Kaplan, P. Cros and C. Mabilat. 1999, Mycobacterium species identification and rifampin resistance testing with high-density DNA probe arrays, *J. Clin. Microbiol.* 37: 49–55);

The third is a physico-chemical process, in which lipid component in mycobacteria has been detected by HPLC, GC or mass spectrophotometer. This method is very specific but rquires expensive equipments;

The fourth is a method of detecting mycobacteria composition by serological method. This method uses a coagulation reaction of latex particles or blood corpuscles adsorbed with antibody to mycobacterial antigen or enzyme-linked immunological method in which enzyme is linked with antibody. It is, however, very sensitive only to be proceeded within a limited place. Further, it is difficult for this method to distinguish present infection from previous infection;

The next method to detect mycobacteria consists of infecting mycobacteria with mycobacteriophage L5 inserted with luciferase gene, and inspecting luminescence by luciferin in medium (W. R. Jacobs, R. G. Barletta, R. Udani, J. Chan, G. Kalkut, G. Sosne, T. Kieser, G. J. Sarkis, G. F. Hatful, and B. R. Bloom. 1993, *Science* 260: 819–822); and The last is a method of detecting and identifying mycobacteria by hybridization of oligonucleotide (A. Troesch, H. Nguyen, C. G. Miyada, S. Desvarenne, T. R. Gingeras, P. M. Kaplan, P. Cros and C. Mabilat. 1999. *J. Clin. Microbiol* 37: 49–55).

Besides *Mycobacierium avium* complex (MAC) described above, *M. Fortuitum, M. chelonae* complex, *M. terrae* and *M. vaccae* are also known as non-tuberculosis mycobacteria. Among them, *M. chelonae* complex are classified into *M. chelonae* and *M. abscessus*, and there is no means to distinguish one from the other at present.

SUMMARY OF THE INVENTION

To solve the problems in the prior method of detection and identification of mycobacteria, it is an objective of the present invention to provide specific oligonucleotides as probes or primers for PCR which can be used to detect mycobacteria, to distinguish TB complex from NTM, and to identify species of mycobacteria with an accuracy and effectiveness.

To accomplish the above objective, the present invention provides a DNA of ITS (Internal Transcribed Spacer region) of *Mycobacterium fortuitum, Mycobacterium chelonae, Mycobacterium abscessus, Mycobacterium vaccae, Mycobacterium flavescens, Mycobacterium asiaticum, Mycobacterium porcinum, Mycobacterium acapulcensis* and *Mycobacterium diernhoferi* genes set forth in SEQ ID NOs: 1 to 9.

Further, the present invention provides, as a primer for PCR or a probe for hybridization, an oligonucleotide for detection of mycobacteria set in forth in one of SEQ ID NOs: 10 to 14;

an oligonucleotide for distinction of TB complex from NTB among mycobacteria set in forth in one of SEQ ID NOs: 15 to 23;

an oligonucleotide for detection and identification of MAC (*Mycobacterium avium* and *Mycobacterium intracellulare*) set in forth in one of SEQ ID NOs: 24 to 27;

an oligonucleotide for detection and identification of *Mycobacterium fortuitum* set in forth in one of SEQ ID NOs: 28 to 38;

an oligonucleotide for detection and identification of *Mycobacterium chelonae* set in forth in one of SEQ ID NOs: 39 to 46;

an oligonucleotide for detection and identification of *Mycobacterium abscessus* set in forth in one of SEQ ID NOs: 47 to 52;

an oligonucleotide for detection and identification of *Mycobacterium vaccae* set in forth in one of SEQ ID NOs: 53 to 64;

an oligonucleotide for detection and identification of *Mycobacterium flavescens* set in forth in one of SEQ ID NOs: 65 to 72;

an oligonucleotide for detection and identification of *Mycobacterium gordonae* set in forth in one of SEQ ID NOs: 73 to 77;

an oligonucleotide for detection and identification of *Mycobacterium terrae* set in forth in one of SEQ ID NOs: 78 to 100;

an oligonucleotide for detection and identification of *Mycobacterium scrofulaceum* set in forth in one of SEQ ID NOs: 101 to 108;

an oligonucleotide for detection and identification of *Mycobacterium kansasii* set in forth in one of SEQ ID NOs: 109 to 112;

an oligonucleotide for detection and identification of *Mycobacterium szulgai* set in forth in one of SEQ ID NOs: 113 to 116;

an oligonucleotide for detection and identification of *Mycobacterium marinum* and *Mycobacterium ulcerans* set in forth in one of SEQ ID NOs: 117 to 119;

an oligonucleotide for detection and identification of *Mycobacterium gastri* set in forth in one of SEQ ID NOs: 120 to 123;

an oligonucleotide for detection and identification of *Mycobacterium xenopi* set in forth in one of SEQ ID NOs: 124 to 133;

an oligonucleotide for detection and identification of *Mycobacterium genavense* set in forth in one of SEQ ID NOs: 134 to 141;

an oligonucleotide for detection and identification of *Mycobacterium malmoense* set in forth in one of SEQ ID NOs: 142 to 146;

an oligonucleotide for detection and identification of *Mycobacterium simiae* set in forth in one of SEQ ID NOs: 147 to 153;

an oligonucleotide for detection and identification of *Mycobacterium smegmatis* set in forth in one of SEQ ID NOs: 154 to 165;

an oligonucleotide for detection and identification of *Mycobacterium shimoidei* set in forth in one of SEQ ID NOs: 166 to 172;

an oligonucleotide for detection and identification of *Mycobacterium habana* set in forth in one of SEQ ID NOs: 173 to 180;

an oligonucleotide for detection and identification of *Mycobacterium farcinogen* set in forth in one of SEQ ID NOs: 181 to 189;

an oligonucleotide for detection and identification of *Mycobacterium asiaticum* set in forth in one of SEQ ID NOs: 190 to 193;

an oligonucleotide for detection and identification of *Mycobacterium porcinum* set in forth in one of SEQ ID NOs: 194 to 205;

an oligonucleotide for detection and identification of *Mycobacterium acapulcensis* set in forth in one of SEQ ID NOs: 206 to 215;

an oligonucleotide for detection and identification of *Mycobacterium diernhoferi* set in forth in one of SEQ ID NOs: 216 to 227;

an oligonucleotide for detection and identification of *Mycobacterium paratuberculosis* set in forth in one of SEQ ID NOs: 228 to 240; and an oligonucleotide for detection of Mycobacteria sp. set in forth in SEQ ID NO: 241.

In the prior method of detecting and identifying mycobacteria using PCR, only one or two strains can be detected. According to the present invention, however, almost all of mycobacteria strains can be detected and identified, since primers and probes of the present invention have been designed form DNA sequences of ITS of mycobacteria. ITS has more polymorphic region than 16S rRNA has and ITS also has conserved region, therefore, it is highly effective as a target DNA for distinction of genotype (Gurtler, V., and V. A. Stanisich, 1996, New approaches to typing and identification of bacteria using the 16S–23S rDNA spacer region. *Microbiol.* 142: 3–16).

The inventors identified DNA sequences of ITS of non-tuberculosis mycobacteria whose DNA had not yet been sequenced, such as *Mycobacterium fortuitum, Mycobacterium chelonae, Mycobacterium abscessus, Mycobacterium vaccae, Mycobacterium flavescens, Mycobacterium asiaticum, Mycobacterium porcinum, Mycobacterium acapulcensis* and *Mycobacterium diernhoferi*. Using the DNA sequences, oligonucleotides for primers or probes have been designed for detecting and identifying the mycobacteria. Further, referring to the information on DNA sequence of other mycobacteria disclosed in GenBank, and analyzing the information with multi-alignment and blast, distinctive regions of polymorphism were selected to design oligonucleotides for primers or probes to detect and identify mycobacteria. The oligonucleotides have been confirmed to detect and identify mycobacteria by specific hybridization and amplification with species-specific and genus-specific primers of PCR.

That is, the oligonucleotide probes of the present invention, attached to solid substrate, are hybridized only with nucleotide sequence in ITS of specific mycobacteria, and therefore, they can detect and identify the specific mycobacteria sensitively. Further, the oligonucleotide primers of identical nucleotide sequence with the above probes can also detect and identify the specific mycobacteria by amplification in PCR. Using the oligonucleotide primers or probes made from ITS of mycobacteria, it is possible to detect mycobacteria, distinguish TB complex from NTM, and identify mycobacteria species accurately and effectively.

BRIEF DESCRIPTION OF THE DRAWINGS

The above and other objects, features, and advantages of the present invention will be apparent from the following detailed description of the preferred embodiments of the invention in conjunction with the accompanying drawings, in which.

BEST MODE FOR CARRYING OUT THE INVENTION

Now, preferred embodiments of the present invention will be described with reference to the accompanying drawings.

EXAMPLE 1

Culture of Mycobacteria and Separation of Genome DNA

Standard strains of mycobacteria were obtained from KCTC (Korean Collection for Type Culture) and ATCC (American Type Culture Collection), clinical strains were obtained from The Korean National Tuberculosis Association, National Masan Tuberculosis Hospital and Pusan National University Hospital. The strains were stored and cultured under the management of clinical microbiology specialist in Pusan National University Hospital. The mycobacteria and pathogens used in the examples are shown in Table 8.

Mycobacteria DNA was extracted by the following processes: Mycobacteria were cultured on Ogawa medium. A loopful of cultured strain was put in eppendorf tube, mixed with 200 μl of InstaGene matrix (Bio-Rad Co.) and incubated at 56° C. for 30 minutes. After 10 minutes' vortex mixing, the mixture was placed at 100° C. for 8 minutes. After another 10 minutes' vortex mixing, the mixture was centrifuged at 12,000 rpm for 3 minutes. The supematant was moved to another tube and stored at −20° C. 2 μl of the DNA solution of each strain was used in the succeeding PCR.

EXAMPLE 2

Manufacture of Primers for Amplifying ITS of Mycobacteria

Figure 1:
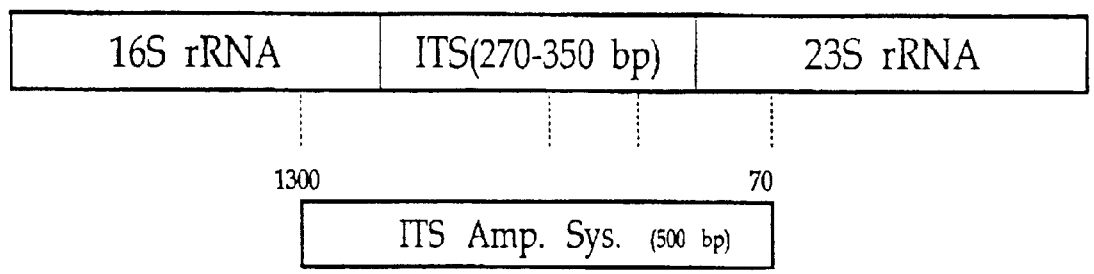
FIG. 1 is a schematic diagram showing ITS of mycobacteria and primers used to amplify the ITS by PCR.

The ITS of mycobacteria and primers used to amplify the ITS by PCR were illustrated in FIG. 1. The primers for amplifying ITS of mycobacteria were constructed from several section of conserved regions of 16S rRNA and 23S rRNA of mycobacteria. DNA sequences of 16S and 23S rRNA of mycobacteria disclosed in GenBank were analyzed with multialignment and blast search. The primers were designed to amplify selectively about 500 bp of ITS region with a part of 16S rRNA and 23S rRNA and have sequences set in forth in SEQ ID NOs: 242 (ITSF) and 243 (ITSR). All the primers used in Examples were manufactured by the concentration of 50 nmol with Perkin-Elmer DNA Synthesizer by BioBasic (Canada).

EXAMPLE 3

PCR and Identification of Products

2 μl of the DNA solution obtained in Example 1 was used in PCR. Reaction solution included: 500 mM KCl, 100 mM Tris HCl (pH 9.0), 1% Triton X-100, 0.2 mM dNTP (dATP, dGTP, dTTP and dCTP), 1.5 mM $MgCl_2$, 1 pmol of primer, 1 U of Taq DNA polymerase (Bio Basic Inc.). After denaturated at 94° C. for 5 minutes, the solution was reacted 30 cycles of denaturation at 94° C. for 1 minute, annealing at 60° C. for 1 minute, and elongation at 72° C. for 1 minute. The samples were incubated further for 10 minutes at 72° C. for complete elongation. After the reaction, the PCR products were identified by electrophoresis on 1.5% agarose gel. As expected from the information of GenBank, the ITS amplified using the conserved primers of 16S rRNA and 23S rRNA was about 500 bp.

Figure 2:
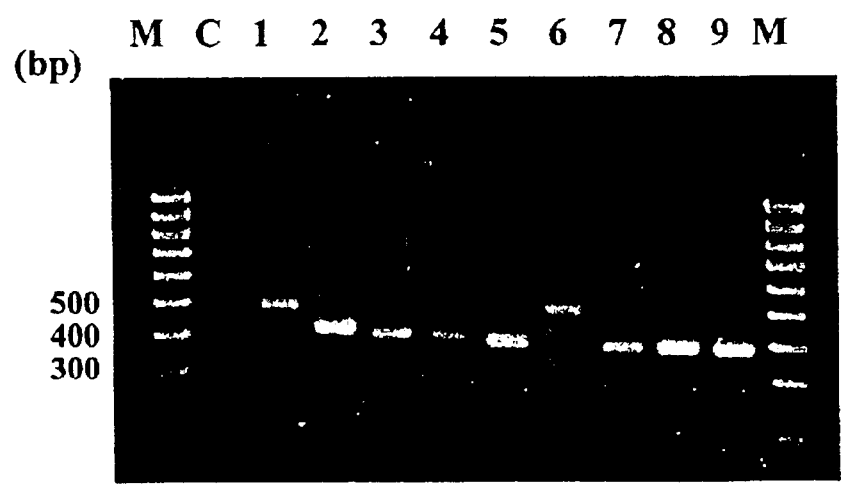
FIG. 2 is a photograph showing the result of electrophoresis after PCR using several mycobacteria strains and a pair of primers for ITS amplification including a part of 16S rRNA and 23S rRNA of mycobacteria.

FIG. 2 is a photograph showing the result of electrophoresis after PCR using several mycobacteria strains and a pair of primers for ITS amplification including a part of 16S rRNA and 23S rRNA of mycobacteria. In this figure, M means molecular weight mark having intervals of 100 bp, C is a control group, lanes 1 to 9 indicate, in turn, *M. fortuitum, M. chelonae, M. intracellularae, M. avium, M. tuberculosis, M. agri, M. kansasii, M. gordonae*, and *M. tuberculosis* H37Rv. It can be noted that all mycobacteria of lanes 1 to 9 have amplification of ITS gene except control group C.

EXAMPLE 4

Determination of DNA Sequence of Mycobacteria ITS

After the identification of PCR products, the reactants of *M. fortuitum, M. chelonae, M. abscessus, M. vaccae, M. flavescens, M. asiaticum, M. porcinum, M. acapulcensis* and *M. diernhoferi*, whose DNA sequences of ITS have not yet been determined, were amplified by PCR. The PCR products were used directly in determining DNA sequence of ITS.

DNA was used by the concentration of 200 μmol. DNA sequence was determined by dye terminator method using universal primer M13 with DNA auto sequencer (Perkin-Elmer, ABI prim 377 sequencer).

SEQ ID NOs 1 to 9 indicate DNA sequences of ITS of *Mycobacterium fortuitum, Mycobacterium chelonae, Mycobacierium abscessus, Mycobacterium vaccae, Mycobacterium flavescens, Mycobacterium asiaticum, Mycobacterium porcinum, Mycobacterium acapulcensis* and *Mycobacterium diernhoferi*, in turn,

EXAMPLE 5

Design and Synthesis of Oligonucleotide Primer

Each primer of about 20 bp was designed from DNA sequences of ITS of *Mycobacterium fortuitum, Mycobacterium cheloniae, Mycobacierizim abscessus, Mycobacterium vaccae, Mycobacterium flavescens, Mycobacterium* asiaticum, *Mycobacterium porcinum, Mycobacterium acapulcensis* and *Mycobacterium diernhoferi*, obtained in Example 4, and compared with DNA sequences of ITS of other mycobacteria obtained from GenBank by multialignment and blast.

Based on the result, conservative DNA sequences of mycobacteria ITS were designed as primers or probes for detection of mycobacteria, and DNA sequences of high polymorphism were designed as species-specific primers or probes. Tables 1 to 7 depict the designed primers or probes with their position and SEQ ID Nos.

TABLE 1

| Target Strain | Probe Name | Position in ITS | SEQ ID NO. |
|---|---|---|---|
| Mycobacteria | MYC1 | Variable to the | 10 |
|  | MYC2 | species | 11 |
|  | MYC3 |  | 12 |
|  | MYC4 |  | 13 |
|  | MYC5 |  | 14 |
| TB complex | MTB1 | 166–185 | 15 |
|  | MTB2 | 65–84 | 16 |
|  | MTB3 | 20–39 | 17 |
|  | MTB4 | 41–60 | 18 |
|  | MTB5 | 60–79 | 19 |
|  | MTB6 | 81–100 | 20 |
|  | MTB7 | 125–144 | 21 |
|  | MTB8 | 139–158 | 22 |
|  | MTB9 | 203–222 | 23 |
| *M. avium - M. intracellularae* (MAC) | MAC1 | 241–260 | 24 |
|  | MAC2 | 142–161 | 25 |
|  | MAC3 | 92–111 | 26 |
|  | MAC4 | 117–136 | 27 |
| *M. fortuitum* | FOR1 | 40–59 | 28 |
|  | FOR2 | 44–63 | 29 |
|  | FOR3 | 64–83 | 30 |
|  | FOR4 | 78–97 | 31 |
|  | FOR5 | 89–108 | 32 |
|  | FOR6 | 109–128 | 33 |
|  | FOR7 | 114–133 | 34 |
|  | FOR8 | 134–153 | 35 |
|  | FOR9 | 157–176 | 36 |
|  | FOR10 | 246–265 | 37 |
|  | FOR11 | 289–308 | 38 |
| *M. chelonae* | CHE1 | 11–30 | 39 |
|  | CHE2 | 29–48 | 40 |
|  | CHE3 | 58–77 | 41 |
|  | CHE4 | 78–97 | 42 |
|  | CHE5 | 109–128 | 43 |
|  | CHE6 | 132–151 | 44 |
|  | CHE7 | 171–190 | 45 |
|  | CHE8 | 246–265 | 46 |

TABLE 2

| Target Strain | Probe Name | Position in ITS | SEQ ID NO. |
|---|---|---|---|
| *M. abscessus* | ABC1 | 37–56 | 47 |
|  | ABC2 | 55–74 | 48 |
|  | ABC3 | 247–266 | 49 |
|  | ABC4 | 263–282 | 50 |
|  | ABC5 | 270–289 | 51 |
|  | ABC6 | 261–280 | 52 |
| *M. vaccae* | VAC1 | 18–37 | 53 |
|  | VAC2 | 38–57 | 54 |
|  | VAC3 | 58–77 | 55 |
|  | VAC4 | 118–137 | 56 |
|  | VAC5 | 138–157 | 57 |
|  | VAC6 | 158–177 | 58 |
|  | VAC7 | 178–197 | 59 |
|  | VAC8 | 199–218 | 60 |
|  | VAC9 | 219–238 | 61 |
|  | VAC10 | 265–284 | 62 |
|  | VAC11 | 298–317 | 63 |
|  | VAC12 | 321–340 | 64 |

TABLE 2-continued

| Target Strain | Probe Name | Position in ITS | SEQ ID NO. |
|---|---|---|---|
| *M. flavescens* | FLA1 | 12–31 | 65 |
|  | FLA2 | 32–51 | 66 |
|  | FLA3 | 52–71 | 67 |
|  | FLA4 | 72–91 | 68 |
|  | FLA5 | 105–124 | 69 |
|  | FLA6 | 125–144 | 70 |
|  | FLA7 | 173–192 | 71 |
|  | FLA8 | 278–297 | 72 |
| *M. gordonae* | GOR1 | 84–103 | 73 |
|  | GOR2 | 249–268 | 74 |
|  | GOR3 | 216–235 | 75 |
|  | GOR4 | 201–220 | 76 |
|  | GOR5 | 223–242 | 77 |

TABLE 3

| Target Strain | Probe Name | Position in ITS | SEQ ID NO. |
|---|---|---|---|
| *M. terrae* | TER1 | 178–197 | 78 |
|  | TER2 | 237–256 | 79 |
|  | TER3 | 24–43 | 80 |
|  | TER4 | 70–89 | 81 |
|  | TER5 | 89–108 | 82 |
|  | TER6 | 102–121 | 83 |
|  | TER7 | 122–141 | 84 |
|  | TER8 | 142–161 | 85 |
|  | TER9 | 162–181 | 86 |
|  | TER10 | 182–201 | 87 |
|  | TER11 | 202–221 | 88 |
|  | TER12 | 222–241 | 89 |
|  | TER13 | 238–257 | 90 |
|  | TER14 | 307–326 | 91 |
|  | TER15 | 322–341 | 92 |
|  | TER16 | 342–361 | 93 |
|  | TER17 | 362–381 | 94 |
|  | TER18 | 382–401 | 95 |
|  | TER19 | 12–21 | 96 |
|  | TER20 | 31–50 | 97 |
|  | TER21 | 52–71 | 98 |
|  | TER22 | 72–91 | 99 |
|  | TER23 | 82–101 | 100 |
| *M. scrofulaceum* | SCO1 | 118–137 | 101 |
|  | SCO2 | 131–150 | 102 |
|  | SCO3 | 210–229 | 103 |
|  | SCO4 | 84–103 | 104 |
|  | SCO5 | 152–171 | 105 |
|  | SCO6 | 200–219 | 106 |
|  | SCO7 | 221–240 | 107 |
|  | SCO8 | 241–260 | 108 |
| *M. kansasii* | KAN1 | 35–54 | 109 |
|  | KAN2 | 238–257 | 110 |
|  | KAN3 | 83–102 | 111 |
|  | KAN4 | 214–233 | 112 |

TABLE 4

| Target Strain | Probe Name | Position in ITS | SEQ ID NO. |
|---|---|---|---|
| *M. szulgai* | SZU1 | 124–143 | 113 |
|  | SZU2 | 209–228 | 114 |
|  | SZU3 | 227–246 | 115 |
|  | SZU4 | 247–166 | 116 |
| *M. marinum* and *M. ulcerans* | MAR-ULC1 | 85–104 | 117 |
|  | MAR-ULC2 | 128–147 | 118 |
|  | MAR-ULC3 | 224–243 | 119 |
| *M. gastri* | GAS1 | 85–104 | 120 |
|  | GAS2 | 145–164 | 121 |
|  | GAS3 | 133–152 | 122 |
|  | GAS4 | 239–258 | 123 |
| *M. xenopi* | XEN1 | 190–209 | 124 |
|  | XEN2 | 1–20 | 125 |
|  | XEN3 | 21–40 | 126 |

TABLE 4-continued

| Target Strain | Probe Name | Position in ITS | SEQ ID NO. |
|---|---|---|---|
|  | XEN4 | 41–60 | 127 |
|  | XEN5 | 61–80 | 128 |
|  | XEN6 | 81–100 | 129 |
|  | XEN7 | 121–140 | 130 |
|  | XEN8 | 141–160 | 131 |
|  | XEN9 | 201–220 | 132 |
|  | XEN10 | 221–240 | 133 |
| M. genavense | GEN1 | 190–209 | 134 |
|  | GEN2 | 85–104 | 135 |
|  | GEN3 | 131–150 | 136 |
|  | GEN4 | 147–166 | 137 |
|  | GEN5 | 186–205 | 138 |
|  | GEN6 | 206–225 | 139 |
|  | GEN7 | 226–245 | 140 |
|  | GEN8 | 240–265 | 141 |
| M. malmoense | MAL1 | 203–222 | 142 |
|  | MAL2 | 29–48 | 143 |
|  | MAL3 | 136–155 | 144 |
|  | MAL4 | 222–241 | 145 |
|  | MAL5 | 242–261 | 146 |
| M. simiae | SIM1 | 83–102 | 147 |
|  | SIM2 | 129–148 | 148 |
|  | SIM3 | 208–227 | 149 |
|  | SIM4 | 22–41 | 150 |
|  | SIM5 | 80–99 | 151 |
|  | SIM6 | 136–155 | 152 |
|  | SIM7 | 241–260 | 153 |

TABLE 5

| Target Strain | Probe Name | Position in ITS | SEQ ID NO. |
|---|---|---|---|
| M. smegmatis | SMEG1 | 17–36 | 154 |
|  | SMEG2 | 37–56 | 155 |
|  | SMEG3 | 57–76 | 156 |
|  | SMEG4 | 77–96 | 157 |
|  | SMEG5 | 97–116 | 158 |
|  | SMEG6 | 117–136 | 159 |
|  | SMEG7 | 137–156 | 160 |
|  | SMEG8 | 157–176 | 161 |
|  | SMEG9 | 177–196 | 162 |
|  | SMEG10 | 193–212 | 163 |
|  | SMEG11 | 61–80 | 164 |
|  | SMEG12 | 112–131 | 165 |
| M. shimoidei | SHI1 | 89–108 | 166 |
|  | SHI2 | 20–39 | 167 |
|  | SHI3 | 70–89 | 168 |
|  | SHI4 | 97–116 | 169 |
|  | SHI5 | 135–154 | 170 |
|  | SHI6 | 224–243 | 171 |
|  | SHI7 | 244–263 | 172 |
| M. habana | HAB1 | 86–105 | 173 |
|  | HAB2 | 17–36 | 174 |
|  | HAB3 | 51–70 | 175 |
|  | HAB4 | 81–100 | 176 |
|  | HAB5 | 134–153 | 177 |
|  | HAB6 | 175–194 | 178 |
|  | HAB7 | 200–219 | 179 |
|  | HAB8 | 242–261 | 180 |
| M. farcinogen | FAR1 | 122–141 | 181 |
|  | FAR2 | 111–130 | 182 |
|  | FAR3 | 22–41 | 183 |
|  | FAR4 | 48–67 | 184 |
|  | FAR5 | 76–95 | 185 |
|  | FAR6 | 108–127 | 186 |
|  | FAR7 | 114–133 | 187 |
|  | FAR8 | 275–294 | 188 |
|  | FAR9 | 295–314 | 189 |

TABLE 6

| Target Strain | Probe Name | Position in ITS | SEQ ID NO. |
|---|---|---|---|
| M. asiaticum | ASI1 | 82–101 | 190 |
|  | ASI2 | 145–164 | 191 |
|  | ASI3 | 189–208 | 192 |
|  | ASI4 | 274–293 | 193 |
| M. porcinum | POR1 | 45–64 | 194 |
|  | POR2 | 13–32 | 195 |
|  | POR3 | 67–86 | 196 |
|  | POR4 | 91–110 | 197 |
|  | POR5 | 115–134 | 198 |
|  | POR6 | 137–156 | 199 |
|  | POR7 | 164–183 | 200 |
|  | POR8 | 194–213 | 201 |
|  | POR9 | 221–240 | 202 |
|  | POR10 | 273–292 | 203 |
|  | POR11 | 298–317 | 204 |
|  | POR12 | 325–344 | 205 |
| M. acapulcensis | ACA1 | 66–85 | 206 |
|  | ACA2 | 112–131 | 207 |
|  | ACA3 | 132–151 | 208 |
|  | ACA4 | 178–197 | 209 |
|  | ACA5 | 198–217 | 210 |
|  | ACA6 | 219–238 | 211 |
|  | ACA7 | 242–261 | 212 |
|  | ACA8 | 262–281 | 213 |
|  | ACA9 | 318–337 | 214 |
|  | ACA10 | 350–369 | 215 |
| M. diernhoferi | DIE1 | 16–35 | 216 |
|  | DIE2 | 36–55 | 217 |
|  | DIE3 | 62–81 | 218 |
|  | DIE4 | 103–122 | 219 |
|  | DIE5 | 154–173 | 220 |
|  | DIE6 | 175–194 | 221 |
|  | DIE7 | 195–214 | 222 |
|  | DIE8 | 232–251 | 223 |
|  | DIE9 | 261–280 | 224 |
|  | DIE10 | 282–301 | 225 |
|  | DIE11 | 304–323 | 226 |
|  | DIE12 | 344–363 | 227 |

TABLE 7

| Target Strain | Probe Name | Position in ITS | SEQ ID NO. |
|---|---|---|---|
| M. para- | PARA1 | 7–26 | 228 |
| tuberculosis | PARA2 | 30–49 | 229 |
|  | PARA3 | 40–59 | 230 |
|  | PARA4 | 50–69 | 231 |
|  | PARA5 | 71–90 | 232 |
|  | PARA6 | 83–102 | 233 |
|  | PARA7 | 103–122 | 234 |
|  | PARA8 | 135–154 | 235 |
|  | PARA9 | 157–176 | 236 |
|  | PARA10 | 178–197 | 237 |
|  | PARA11 | 198–217 | 238 |
|  | PARA12 | 219–238 | 239 |
|  | PARA13 | 241–260 | 240 |
| M. sp | SP1 | 225–244 | 241 |

EXAMPLE 6

Result of PCR Using Primers for Detecting Mycobacteria

Genus-specific primers, designed from conserved DNA sequence in mycobacteria were used for detecting mycobacteria. Among the primers manufactured from the ITS sequence of 270–350 bp, a pair of primers, ITSF (SEQ ID NO. 242) and MYC2 (SEQ ID NO. 11) were used to proceed PCR. As a result, amplified nucleotides of about 350 bp were obtained in mycobacteria strains, while no amplification was occurred in *Staphylococcus aureus, Enterococcus faecium* and *Serratia marcescens*. Therefore, it is understood that the primers could be used for detecting mycobacteria.

Figures 3, 4:
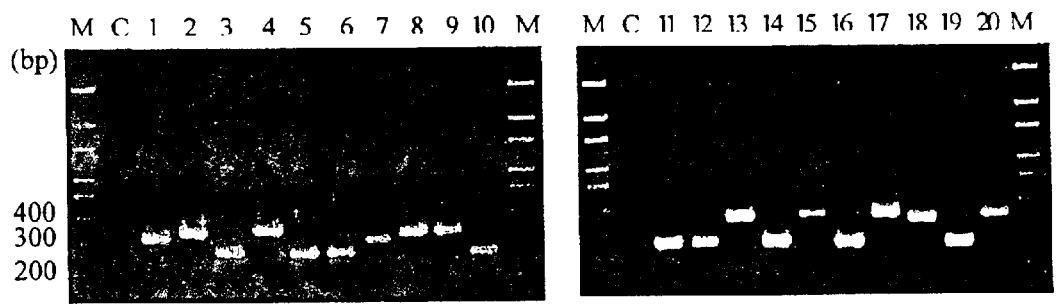
FIG. 3 is a photograph showing the result of electrophoresis after PCR using several mycobacteria strains and a pair of primers (ITSF and MYC2) for detecting mycobacteria.
FIG. 4 is a schematic diagram of multiplex PCR for detecting mycobacteria and simultaneously distinguishing TB complex from NTM.

FIG. 3 is a photograph showing the result of electrophoresis after PCR using several mycobacteria strains and a pair of primers (ITSF and MYC2) for detecting mycobacteria. In this figure, M indicates a size marker of 100 bp ladder; C indicates a negative control; lane 1 indicates *M. abscessus* ATCC 19977; lane 2, *M. agri* ATCC 27406; lane 3, *M. asiaticum* ATCC 25276; lane 4, *M. austroafricanum* ATCC 33464; lane 5, *M. avium* ATCC 25291; lane 6, *M. bovis* ATCC 19210; lane 7, *M. chelonae* ATCC 35752; lane 8, *M. flavescens* ATCC 14474; lane 9, *M. fortuitum* ATCC 6841; lane 10, *M. gordonae* ATCC 14470; lane 11, *M. intracellularae* ATCC 13950; lane 12, *M. kansasii* ATCC 12478; lane 13, *M. phlei* ATCC 354; lane 14, *M. scrofulaceutm* ATCC 19981; lane 15, *M. smegmatis* ATCC 21701; lane 16, *M. szulgai* ATCC 35799; lane 17, *M. terrae* ATCC 15755; lane 18, *M. triviale* ATCC 23292; lane 19, *M. tuberculosis* H37Rv; and lane 20, *M. vaccae* ATCC 15483. It can be seen that all mycobacteria of lanes 1 to 20 show ITS amplification except negative control C.

Table 8 shows the result of PCR using a pair of primers (ITSF and MYC2) for detecting mycobacteria. In this table, + indicates amplification occurred and – indicates no amplification. It can be seen that no amplification has occurred in other strains than mycobacteria.

TABLE 8

| Name of strain | result | Name of strain | result |
|---|---|---|---|
| *M. tuberculosis* H37Rv | + | *M. phlei* ATCC 354 | + |
| *M. bovis* ATCC 19210 | + | *Aeromonas hydrophila* | – |
| *M. avium* ATCC 25291 | + | *Burkholderia cepacia* | – |
| *M. intracellulare* ATCC 13950 | + | *Candida albicans* | – |
| *M. abscessus* ATCC 19977 | + | *Citrobacter freundii* | – |
| *M. chelonae* ATCC 35752 | + | *Enterobacter aerogenes* | – |
| *M. flavescens* ATCC 14474 | + | *Enterobacter cloacae* | – |
| *M. fortuitum* ATCC 6841 | + | *Enterococcus faecalis* | – |
| *M. gastri* ATCC 15754 | + | *Enterococcus faecium* | – |
| *M. genavense* ATCC 51233 | + | *Enterococcus raffinosis* | – |
| *M. gordonae* ATCC 14470 | + | *Escherichia coli* | – |
| *M. kansasii* ATCC 12478 | + | *Klebsiella pneumoniae* | – |
| *M. malmoense* ATCC 29571 | + | *Plesiomonas shigelloides* | – |
| *M. scrofulaceum* ATCC 19981 | + | *Proteus mirabilis* | – |
| *M. simiae* ATCC 25275 | + | *Proteus vulgaris* | – |
| *M. smegmatis* ATCC 21701 | + | *Providencia rettgeri* | – |
| *M. szulgai* ATCC 35799 | + | *Pseudomonas aeruginosa* | – |
| *M. terrae* ATCC 15755 | + | *Rahnella aquatilis* | – |
| *M. vaccae* ATCC 15483 | + | *Salmonella spp.* | – |
| *M. xenopi* ATCC 19250 | + | *Serratia marcescens* | – |
| *M. marinum* ATCC 927 | + | *Shewanella putrefaciens* | – |
| *M. ulcerance* ATCC 19423 | + | *Shigella flexneri* | – |
| *M. porcinum* ATCC 33776 | + | *Shigella sonnei* | – |
| *M. asiaticum* ATCC 25276 | + | *Staphylococcus epidermidis* | – |
| *M. acapulcensis* ATCC 14473 | + | *Staphylococcus aureus* | – |
| *M. diernhoferi* ATCC 19340 | + | *Streptococcus agalactiae* | – |
| *M. agri* ATCC 27406 | + | *Streptococcus intermidius* | – |
| *M. austroafricanum* ATCC 33464 | + | *Streptococcus pneumoniae* | – |
| *M. triviale* ATCC 23292 | + | *Vibrio parahemolyticus* | – |

EXAMPLE 7

Result of PCR Using Primers for TB Complex

Test for identifying each strain using the oligonucleotide primers manufactured in the previous Examples was confirmed by amplification in PCR. For identifying TB complex, multiplex PCR was carried using a pair of primers (ITSF and MYC2) for detecting mycobacteria and a pair of primers (MTB2 and MYC2; SEQ ID Nos. 16 and 11) for distinguishing TB complex from NTM.

FIG. 4 is a schematic diagram of multiplex PCR for detecting mycobacteria and simultaneously distinguishing TB complex from NTM.

Figure 5:
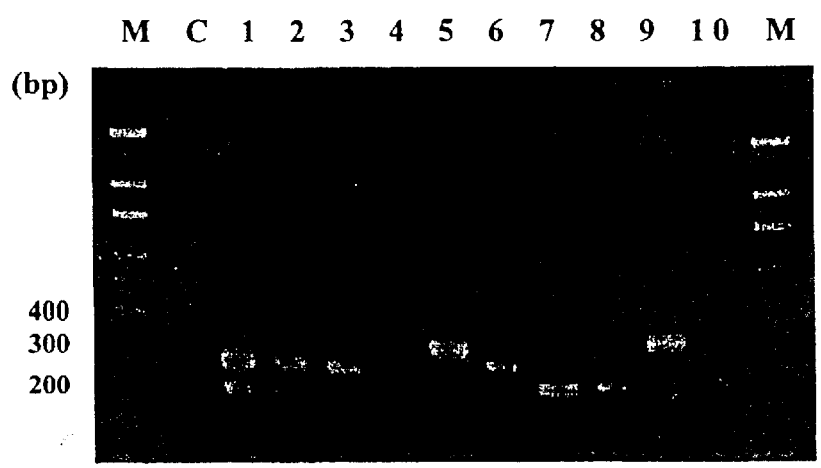
FIG. 5 is a photograph showing the result of electrophoresis after multiplex PCR using a pair of primers (ITSF and MYC2) for detecting mycobacteria and a pair of primers (MTB2 and MYC2) for distinguishing TB complex from NTM.

FIG. 5 is a photograph showing the result of electrophoresis after multiplex PCR using a pair of primers (ITSF and MYC2) for detecting mycobacteria and a pair of primers (MTB2 and MYC2) for distinguishing TB complex from NTM. In this figure, M indicates a size marker of 100 bp ladder; C indicates a negative control; lanes 1 and 2 indicate TB complex, *M. tuberculosis* H37Rv and *M. bovis*, respectively; and lanes 3 to 10 indicate *M. avium, M. intracellularae, M. fortuitum, M. chelonae, M. gordonae, M. szulgai, M. terrae* and *M. scrofulaceum* ATCC 19981, in turn. In lanes 1 and 2 of TB complex, two bands are formed by double amplification due to primers for detecting mycobacteria and primers for TB complex, while in the other lanes of NTM strains, only one band is formed, which confirms single amplification.

EXAMPLE 8

Result of PCR Using Primers for Identifying NTM Strains

PCR was carried out using species-specific primers manufactured from DNA sequence of polymorphic site of each strain for identifying NTM species.

Specifically, after selecting SEQ ID NOs. 16 and 21 for *M. tuberculosis* H37Rv and *M. bovis*, SEQ ID NOs. 24 and 27 for *M. avium* and *M. intracellularae*, SEQ ID NOs. 29 and 37 for *M. fortuitum*, SEQ ID NOs. 41 and 44 for *M. chelonae*, SEQ ID NOs. 48 and 49 for *M. abscessus*, SEQ ID NOs. 55 and 63 for *M. vaccae*, SEQ ID NOs. 66 and 72 for *M. flavescens*, SEQ ID NOs. 73 and 75 for *M. gordonae*, SEQ ID NOs. 88 and 96 for *M. terrae*, SEQ ID NOs. 102 and 103 for *M. scrofulaceum*, SEQ ID NOs. 109 and 110 for *M. kansasii*, SEQ ID NOs. 113 and 114 for *M. szulgai*, SEQ ID NOs. 117 and 119 for *M. marinum* and *M. ulcerans*, SEQ ID NOs. 120 and 123 for *M. gastri*, SEQ ID NOs. 128 and 132 for *M. xenopi*, SEQ ID NOs. 135 and 141 for *M. genavense*, SEQ ID NOs. 143 and 145 for *M. malmoense*, SEQ ID NOs. 147 and 149 for *M. simiae*, and SEQ ID NOs. 154 and 159 for *M. smegmalis*, each mycobacteria was carried out PCR using each pair of primers of which the first has been sense strand and the second has been antisense strand. After the reaction, each resultant was treated by electrophoresis.

Figure 6:
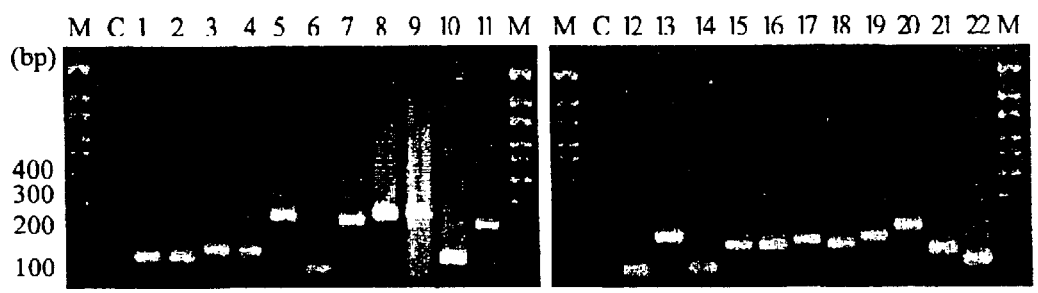
FIG. 6 is a photograph showing the result of electrophoresis after PCR using each mycobacteria and each pair of species-specific primers designed from nucleotide sequence of polymorphic region of each NTM.

FIG. 6 is a photograph showing the result of electrophoresis after PCR using each mycobacteria and each pair of species-specific primers designed from nucleotide sequence of polymorphic region of each NTM. In this figure, M indicates a size marker of 100 bp ladder; C indicates a negative control; lanes 1 and 2 indicate TB complex, *M. tuberculosis* H37Rv and *M. bovis* ATCC 19210, respectively; lanes 3 and 4 indicate *M. avium* ATCC 25291 and *M. intracellularae* ATCC 13950, respectively; lane 5 indicates *M. fortuitum* ATCC 6841; lane 6, *M. chelonae* ATCC 35752; lane 7, *M. abscessus* ATCC 19977; lane 8, *M. vaccae* ATCC 15483; lane 9, *M. flavescens* ATCC 14474; lane 10, *M. gordonae* ATCC 14470; lane 11, *M. terrae* ATCC 15755; lane 12, *M. scrofulaceum* ATCC 19981; lane 13, *M. kansasii* ATCC 12478; lane 14, *M. szulgai* ATCC 35799; lane 15, *M. marinum* ATCC 927; lane 16, *M. ulcerans* ATCC 19423; lane 17, *M. gastri* ATCC 15754; lane 18, *M. xenopi* ATCC 19250; lane 19, *M. genavense* ATCC 1233; lane 20, *M. malmoense* ATCC 29571; lane 21, *M. simiae* ATCC 25275; and lane 22 indicates *M. smegmatis* ATCC 21701. Species-specific amplifications can be seen in lanes 1 to 22.

Figure 7:
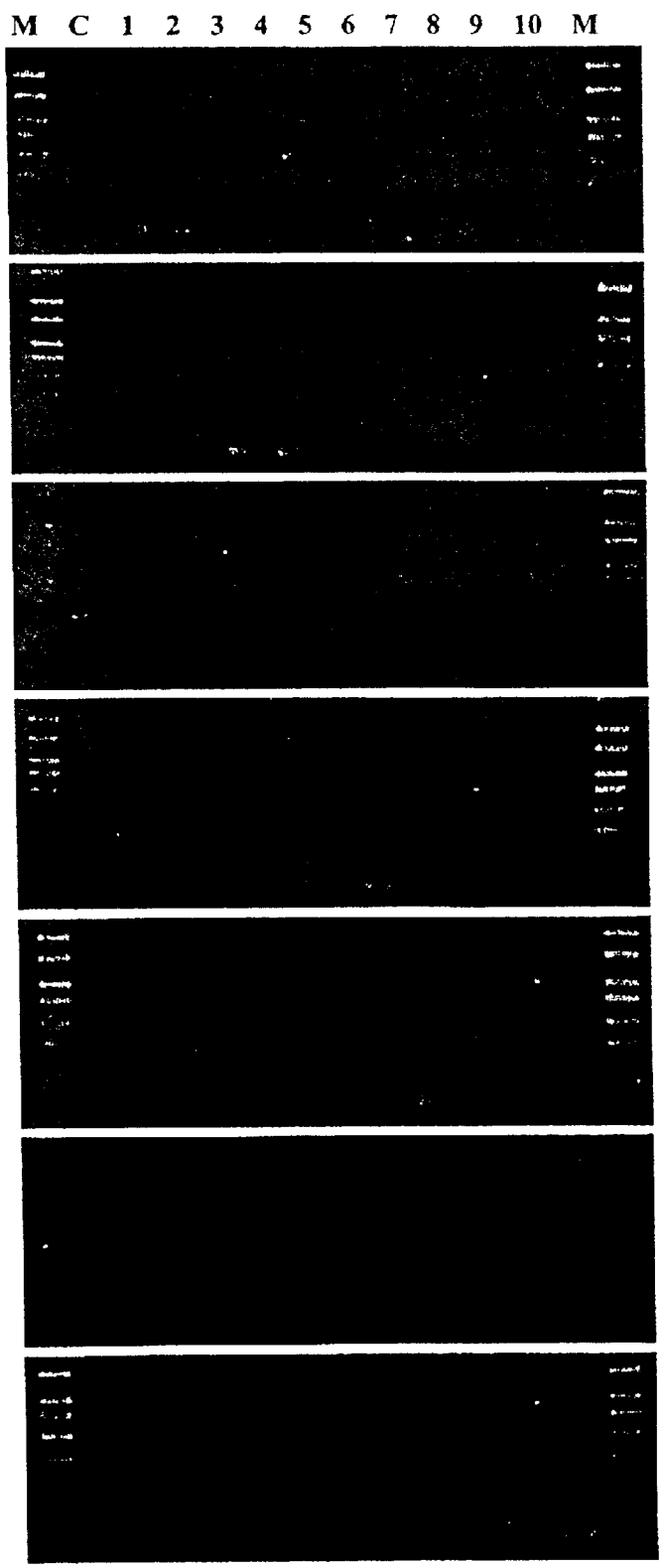
FIG. 7 is a photograph showing the result of electrophoresis after PCR using several mycobacteria and each pair of species-specific primers designed from nucleotide sequence of polymorphic region of each NTM.

FIG. 7 is a photograph showing the result of electrophoresis after PCR using several mycobacteria and each pair of species-specific primers designed from nucleotide sequence of polymorphic region of each NTM. In this figure, the first photograph using the pair of primers (ITSF and MYC2) specific for TB complex shows amplifications in lanes 1 and 2 of *M. tuberculosis* H37Rv and *M. bovis*; the second using the pair of primers (MAC1 and MAC4) specific for *M. avium* and *M. intracellularae* shows amplifications in lanes 3 and 4 of *M. avium* and *M. intracellularae*; the third using the pair of primers (FOR2 and FOR10) specific for *M. fortuitum* shows amplification in lane 5 of *M. fortuitum*; the fourth using the pair of primers (CHE3 and CHE6) specific for *M. chelotiae* shows amplification in lane 6 of *M. chelonae*; the fifth using the pair of primers (GOR1 and GOR2) specific for *M. gordonae* shows amplification in lane 7 of *M. gordonae*; the sixth using the pair of primers (SZU1 and SZU2) specific for *M. szulgai* shows amplification in lane 8 of *M. szulgai*; and the seventh using the pair of primers (SCO1 and SCO2) specific for *M. scrofulaceum* shows amplification in lane 10 of *M. scrofulaceum*. Lane 9 indicates *M. terrae*, which shows no amplification with the above species—specific primer pairs.

Therefore, PCR using each pair of species-specific primers can detect and identify specifically each species of mycobacteria.

INDUSTRIAL APPLICABILITY

As described above, identifying DNA sequences of ITS (Internal Transcribed Spacer region) of non-tuberculosis mycobacteria, *Mycobacterium fortuitum, Mycobacterium chelonae, Mycobacterium abscessus, Mycobacterium vaccae, Mycobacterium flavescens, Mycobacterium asiaticum, Mycobacterium porcinur, Mycobacterium acapulcensis* and *Mycobacterium diernhoferi*, and using the DNA sequences, oligonucleotide primers or probes can been designed for detecting and identifying mycobacteria. Using the primers for PCR or probes for hybridization, it is possible to detect mycobacteria, distinguish TB complex from NTM, and identify mycobacteria species with rapidity and effectiveness. Such detection and identification method makes the diagnosis of complex infection effective, and therefore, it is possible to treat accurately mycobacterial infection including tuberculosis.

While this invention has been described in connection with what is presently considered to be the most practical and preferred embodiments, it is to be understood that the invention is not limited to the disclosed embodiment, but, on the contrary, it is intended to cover various modifications and equivalent arrangements included within the spirit and scope of the appended claims.

What is claimed is:

1. An isolated DNA molecule of an Internal Transcribed Spacer region of *Mycobacterium fortuitum* where said DNA molecule consists of, SEQ ID NO: 1.

2. An oligonucleotide for detection and identification of *Mycobacterium fortuitum* wherein said oligonucltide is selected from the group consisting of SEQ ID NOs: 28 to 38.

3. A method for detecting *Mycobacterium fortuitum* from a sample comprising:

obtaining a sample DNA from the sample;

hybridizing the sample DNA with a DNA primer, the DNA primer is at least one oligonucleotide selected from the group consisting of SEQ ID Nos: 28 to 38, amplifying the sample DNA hybridized with the DNA primer; and detecting and identifying a product of amplification thereby detecting and identifying *Mycobacterium fortuitum*.

* * * * *

SEQUENCE LISTING

<160> NUMBER OF SEQ ID NOS: 243

<210> SEQ ID NO 1
<211> LENGTH: 386
<212> TYPE: DNA
<213> ORGANISM: Mycobacterium fortuitum

<400> SEQUENCE: 1

```
aggagcacca cgaaaagggt tgagacactg ggtcttaccc gagccgtgag gaaccggttg      60
cctgtagtgg gcacggtttg gtgcacaaca aacttttttg actgccagac acactattgg     120
gctttgagac aacaggcccg tgcccctttt gggggggtggc atccggttgc gggtgtcggc    180
gtgttgttgc ctcactttgg tggtggggtg tggtgtttga tttgtggata gtggttgcga    240
gcatctagca cgcagaatcg tgtggtctca ctccttgtgg gtggggctgg ttttgtgtgt    300
tgatgtgcaa tttcttttga aactcatttt tggttttttgt gttgtaagtg tttaagggcg    360
catggtggat gccttggcag gatcca                                        386
```

<210> SEQ ID NO 2
<211> LENGTH: 338
<212> TYPE: DNA
<213> ORGANISM: Mycobacterium chelonae

<400> SEQUENCE: 2

```
aggagcacca tttcccagcc gaatgagctt gggaacataa agcgagtttc tgtagtggtt      60
actcgcttgg tgaatatgtt ttataaatcc tgtccacccc gtggataggt agtcggcaaa     120
acgtcggact gtcaatagaa ttgaaacgct ggcacactgt tgggtcctga ggcaacacat     180
tgtgttgtca ccctgcttgg tggtggggtg tggtctttga cttatggata gtggttgcga    240
gcatctaaca aacctcgctc gtttacgagt gaggttagtt tttgcaattt attagctaag    300
ttcttaaggg cacatggtgg atgccttggc aggatcca                            338
```

<210> SEQ ID NO 3
<211> LENGTH: 317
<212> TYPE: DNA
<213> ORGANISM: Mycobacterium abscessus

<400> SEQUENCE: 3

| | | | | | |
|---|---|---|---|---|---|
| aaggagcacc | atttcccagt | cgaatgaact | agggaacata | aagtaggcat | ctgtagtgga | 60 |
| tatctacttg | gtgaatatgt | tttgtaaatc | ctgtccaccc | cgtggatggg | tagtcggcaa | 120 |
| aacgtcggac | tgtcataaga | attgaaacgc | tggcacactg | ttgggtcccg | aggcaacacg | 180 |
| ttgtgttgtc | accctgcttg | gtggtggggt | gtggactttg | acttctgaat | agtggttgcg | 240 |
| agcatctaaa | catagcctcg | ctcgttttcg | agtggggctg | gtttttgcaa | ttttattagc | 300 |
| taagttctta | agggcgc | | | | | 317 |

<210> SEQ ID NO 4
<211> LENGTH: 429
<212> TYPE: DNA
<213> ORGANISM: Mycobacterium vaccae

<400> SEQUENCE: 4

| | | | | | |
|---|---|---|---|---|---|
| aaggagcacc | acgagaatca | ggcccgccca | catcgtgtgg | gggttcggtg | atctgatcga | 60 |
| ttcgttggat | ggccttcat | ctgtagtgga | tgggggtctg | gtgcacatga | caaacttggc | 120 |
| cgagccggta | gggaatgccg | gcgagggaaa | tcatcagaca | cactattggg | ctttgagaca | 180 |
| acaagcccgt | gccccttttt | tgggggtgg | ctctgcgttg | gcagggtcgg | cgtgttgttg | 240 |
| ccccgctttg | gtggtgggt | gtggtgtttg | attcgtggat | agtggttgcg | agcatctgaa | 300 |
| tgcacagcgc | ttgtggtgtt | gtgtgttcgg | tgtaatgcaa | atttttctga | tactcgcatg | 360 |
| cagtcccttt | tgggggtgt | gtgtgggtga | ctcattttt | ggttttgtgt | tgtaagtgtt | 420 |
| taagggcgc | | | | | | 429 |

<210> SEQ ID NO 5
<211> LENGTH: 379
<212> TYPE: DNA
<213> ORGANISM: Mycobacterium flavescens

<400> SEQUENCE: 5

| | | | | | |
|---|---|---|---|---|---|
| aaggagcacc | atttattgtt | cccccgtccc | cacgtgtgtg | ggatcagtgc | ggttgggaga | 60 |
| tcagtgccgg | gcctgtagtg | ggtttccggt | gggtgcacaa | caaacgtgag | aagtggtgtg | 120 |
| ggaacactgc | tttgaggaat | catcagacac | actattgggc | tttgaggcaa | caggcccgt | 180 |
| gtttccctgg | ccactgtgtg | tggtggggg | tctggtgtcg | ccctgtcttt | ggtggtgggg | 240 |
| tgtggtgttt | gattcgtgga | tagtggttgc | gagcatctga | acaggtggct | cccttttggg | 300 |
| ggttgcttgt | tttgataatg | caattttta | ttcttccgag | aatattttc | tgttttgtgt | 360 |
| tgtaagtgtt | taagggcgc | | | | | 379 |

<210> SEQ ID NO 6
<211> LENGTH: 364
<212> TYPE: DNA
<213> ORGANISM: Mycobacterium asiaticum

<400> SEQUENCE: 6

| | | | | | |
|---|---|---|---|---|---|
| tggatccgac | gaagtcgtaa | caaggtagcc | gtaccggaag | gtgcggctgg | atcacctcct | 60 |
| ttctaaggag | caccacgaaa | gcatcccaat | tggtgggatg | caggccgtgt | ggagttctcg | 120 |
| tctgtagtgg | acgagggctg | ggtgcacaac | aacaagcaag | ccagacacac | tattgggtcc | 180 |

-continued

| | |
|---|---|
| tgagacaaca ctcgggcgct agcacgaagt gttgtccctc catcttggtg gtggggtgtg | 240 |
| gtgtttgaga actggatagt ggttgcgagc atcaactgat cgcgtcgccg ttcgcggtgg | 300 |
| cgtgttcttt tgtgcaattt taaattcttt ggttttgta gtgtttgtaa gtgtctaagg | 360 |
| gcgc | 364 |

<210> SEQ ID NO 7
<211> LENGTH: 402
<212> TYPE: DNA
<213> ORGANISM: Mycobacterium porcinum

<400> SEQUENCE: 7

| | |
|---|---|
| aaggagcacc gattcgattc ccccgccgtc cgcgtagtcg tgggcagtag tgcggttggg | 60 |
| atatttcagc caggacctgt agtgggtgtc tggtgggtgc aaatgacaaa cgttgagccg | 120 |
| gcgcgggaaa gcgttggtga tggaactgct gaacacacta ttgggctttg agacaacagg | 180 |
| cccgtgcccc tttcgggggg tggcattccg ttgggagtgt cggcgtgttg ttgctccgct | 240 |
| ttggtggtgg ggtgtggtgt ttgatttgtg gatagtggtt gcgagcatct agcacgcagt | 300 |
| gtggctgggg gccttcgggt ttccggtctt gttgtgtgtt gatgtgcaat ttcttttgaa | 360 |
| actcattttt ggtttttgtg ttgtaagtgt ttaagggcgc at | 402 |

<210> SEQ ID NO 8
<211> LENGTH: 459
<212> TYPE: DNA
<213> ORGANISM: Mycobacterium acapulcensis

<400> SEQUENCE: 8

| | |
|---|---|
| aaggagcacc agttattttc ccccgccccc acgcctgtgg gatcagttgc ggttgggata | 60 |
| tttagtgcca gcacctgtag tgggtgtttc ggccggtgca cagcaaacgt tgatcgtctg | 120 |
| gtggggaaag ccggcgtga aagattgcca gacacactat tgggctttga dacaacaagc | 180 |
| ccgtcgcctc tttgtcccga gtgtgggata tcggagaagg agcaccacga gacctgttgc | 240 |
| ccgcccacat cgtgtgggag ttcggtgact caggcgattc gggggttggt tgtggttgtc | 300 |
| gccctgcttt ggtggtgggg tgtggtgttt gatttgtgga tagtggttgc gagcatctga | 360 |
| acgcagagac ctgtgtgggt ttttgtgttc tgataatgca atttttattc ttccgagaat | 420 |
| attttttgat ctgttttgtg tgtaagtgtt taagggcgc | 459 |

<210> SEQ ID NO 9
<211> LENGTH: 418
<212> TYPE: DNA
<213> ORGANISM: Mycobacterium diernhoferi

<400> SEQUENCE: 9

| | |
|---|---|
| aaggagcacc acgagacctg ttgcccgccc acatcgtgtg ggagttcggt gactcaggcg | 60 |
| attcgttgga tggcctcaca cctgtagtgg gtgggggtct ggtgcacaac aaactttgag | 120 |
| aaactgccag acacactatt gggctttgag caacaggcc ctgcggtgcc ggactcgttg | 180 |
| gagtcctggt tgccggccgc gagtcccgga agcgattctg gttcggacgg tgtctgttgt | 240 |
| tgctccatct ttggtggtgg ggtgtggtgt ttgatttgtg gatagtggtt gcgagcatct | 300 |
| agcacgcaag aggagtctgg gtttccttcg ggagcccggg ttttttgttgt gtgtgtttga | 360 |
| tgtgcaattt ttttcttcta tttggtttta tctgtgttgt aagtgtttaa gggcgcat | 418 |

<210> SEQ ID NO 10
<211> LENGTH: 20

```
<212> TYPE: DNA
<213> ORGANISM: Artificial Sequence
<220> FEATURE:
<223> OTHER INFORMATION: sequence of probe or primer for detecting
      Mycobacteria

<400> SEQUENCE: 10
tggtggggtg tggtgtttga                                                  20

<210> SEQ ID NO 11
<211> LENGTH: 20
<212> TYPE: DNA
<213> ORGANISM: Artificial Sequence
<220> FEATURE:
<223> OTHER INFORMATION: sequence of probe or primer for detecting
      Mycobacteria

<400> SEQUENCE: 11
tggatagtgg ttgcgagcat                                                  20

<210> SEQ ID NO 12
<211> LENGTH: 20
<212> TYPE: DNA
<213> ORGANISM: Artificial Sequence
<220> FEATURE:
<223> OTHER INFORMATION: sequence of probe or primer for detecting
      Mycobacteria

<400> SEQUENCE: 12
ccatcttggt ggtggggtgt                                                  20

<210> SEQ ID NO 13
<211> LENGTH: 20
<212> TYPE: DNA
<213> ORGANISM: Artificial Sequence
<220> FEATURE:
<223> OTHER INFORMATION: sequence of probe or primer for detecting
      Mycobacteria

<400> SEQUENCE: 13
cacactattg ggccctgagg                                                  20

<210> SEQ ID NO 14
<211> LENGTH: 10
<212> TYPE: DNA
<213> ORGANISM: Artificial Sequence
<220> FEATURE:
<223> OTHER INFORMATION: sequence of probe or primer for detecting
      Mycobacteria

<400> SEQUENCE: 14
aaggagcacc                                                             10

<210> SEQ ID NO 15
<211> LENGTH: 20
<212> TYPE: DNA
<213> ORGANISM: Artificial Sequence
<220> FEATURE:
<223> OTHER INFORMATION: sequence of probe or primer for detecting TB
      complex

<400> SEQUENCE: 15
cactcggact tgttccaggt                                                  20

<210> SEQ ID NO 16
<211> LENGTH: 20
<212> TYPE: DNA
```

```
<213> ORGANISM: Artificial Sequence
<220> FEATURE:
<223> OTHER INFORMATION: sequence of probe or primer for detecting TB
      complex

<400> SEQUENCE: 16
tggtggggcg taggccgtga                                                      20

<210> SEQ ID NO 17
<211> LENGTH: 20
<212> TYPE: DNA
<213> ORGANISM: Artificial Sequence
<220> FEATURE:
<223> OTHER INFORMATION: sequence of probe or primer for detecting TB
      complex

<400> SEQUENCE: 17
ccccaactgg tggggcgtag                                                      20

<210> SEQ ID NO 18
<211> LENGTH: 20
<212> TYPE: DNA
<213> ORGANISM: Artificial Sequence
<220> FEATURE:
<223> OTHER INFORMATION: sequence of probe or primer for detecting TB
      complex

<400> SEQUENCE: 18
ccgtgagggg ttcttgtctg                                                      20

<210> SEQ ID NO 19
<211> LENGTH: 20
<212> TYPE: DNA
<213> ORGANISM: Artificial Sequence
<220> FEATURE:
<223> OTHER INFORMATION: sequence of probe or primer for detecting TB
      complex

<400> SEQUENCE: 19
gtagtgggcg agagccgggt                                                      20

<210> SEQ ID NO 20
<211> LENGTH: 20
<212> TYPE: DNA
<213> ORGANISM: Artificial Sequence
<220> FEATURE:
<223> OTHER INFORMATION: sequence of probe or primer for detecting TB
      complex

<400> SEQUENCE: 20
catgacaaca aagttggcca                                                      20

<210> SEQ ID NO 21
<211> LENGTH: 20
<212> TYPE: DNA
<213> ORGANISM: Artificial Sequence
<220> FEATURE:
<223> OTHER INFORMATION: sequence of probe or primer for detecting TB
      complex

<400> SEQUENCE: 21
caacactcgg acttgttcca                                                      20

<210> SEQ ID NO 22
<211> LENGTH: 20
<212> TYPE: DNA
<213> ORGANISM: Artificial Sequence
```

```
<220> FEATURE:
<223> OTHER INFORMATION: sequence of probe or primer for detecting TB
      complex

<400> SEQUENCE: 22
gttccaggtg ttgtcccacc                                              20

<210> SEQ ID NO 23
<211> LENGTH: 20
<212> TYPE: DNA
<213> ORGANISM: Artificial Sequence
<220> FEATURE:
<223> OTHER INFORMATION: sequence of probe or primer for detecting TB
      complex

<400> SEQUENCE: 23
cgagcatcaa tggatacgct                                              20

<210> SEQ ID NO 24
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium avium complex(MAC)

<400> SEQUENCE: 24
gttcatcgaa atgtgtaatt                                              20

<210> SEQ ID NO 25
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium avium complex(MAC)

<400> SEQUENCE: 25
gtgtggagtc cctccatctt                                              20

<210> SEQ ID NO 26
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium avium complex(MAC)

<400> SEQUENCE: 26
aaatgattgc cagacacact                                              20

<210> SEQ ID NO 27
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium avium complex(MAC)

<400> SEQUENCE: 27
ccctgagaca acactcggtc                                              20

<210> SEQ ID NO 28
<211> LENGTH: 20
<212> TYPE: DNA
<213> ORGANISM: Artificial Sequence
<220> FEATURE:
```

```
<223> OTHER INFORMATION: sequence of probe or primer for detecting
      Mycobacterium fortuitum

<400> SEQUENCE: 28
cgagccgtga ggaaccggtt                                                  20

<210> SEQ ID NO 29
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium fortuitum

<400> SEQUENCE: 29
ccgtgaggaa ccggttgcct                                                  20

<210> SEQ ID NO 30
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium fortuitum

<400> SEQUENCE: 30
gtagtgggca cggtttggtg                                                  20

<210> SEQ ID NO 31
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium fortuitum

<400> SEQUENCE: 31
ttggtgcaca acaaactttt                                                  20

<210> SEQ ID NO 32
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium fortuitum

<400> SEQUENCE: 32 caaactttt tgactgccag                                                   20

<210> SEQ ID NO 33
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium fortuitum

<400> SEQUENCE: 33
acacactatt gggctttgag                                                  20

<210> SEQ ID NO 34
<211> LENGTH: 20
<212> TYPE: DNA
<213> ORGANISM: Artificial Sequence
<220> FEATURE:
<223> OTHER INFORMATION: sequence of probe or primer for detecting
```

Mycobacterium fortuitum

<400> SEQUENCE: 34
ctattgggct ttgagacaac                                          20

<210> SEQ ID NO 35
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium fortuitum

<400> SEQUENCE: 35
aggcccgtgc ccctttttggg                                         20

<210> SEQ ID NO 36
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium fortuitum

<400> SEQUENCE: 36
tggcatccgg ttgcgggtgt                                          20

<210> SEQ ID NO 37
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium fortuitum

<400> SEQUENCE: 37
tagcacgcag aatcgtgtgg                                          20

<210> SEQ ID NO 38
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium fortuitum

<400> SEQUENCE: 38
ggttttgtgt gttgatgtgc                                          20

<210> SEQ ID NO 39
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium chelonae

<400> SEQUENCE: 39
tttcccagcc gaatgagctt                                          20

<210> SEQ ID NO 40
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium chelonae

<400> SEQUENCE: 40
ttgggaacat aaagcgagtt                                               20

<210> SEQ ID NO 41
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium chelonae

<400> SEQUENCE: 41
gttactcgct tggtgaatat                                               20

<210> SEQ ID NO 42
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium chelonae

<400> SEQUENCE: 42
gttttataaa tcctgtccac                                               20

<210> SEQ ID NO 43
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium chelonae

<400> SEQUENCE: 43
gtagtcggca aaacgtcgga                                               20

<210> SEQ ID NO 44
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium chelonae

<400> SEQUENCE: 44
tcaatagaat tgaaacgctg                                               20

<210> SEQ ID NO 45
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium chelonae

<400> SEQUENCE: 45
ggcaacacat tgtgttgtca                                               20

<210> SEQ ID NO 46
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium chelonae ―continued

```
<400> SEQUENCE: 46
taacaaacct cgctcgttta                                              20

<210> SEQ ID NO 47
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium abscessus

<400> SEQUENCE: 47
cataaagtag gcatctgtag                                              20

<210> SEQ ID NO 48
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium abscessus

<400> SEQUENCE: 48
agtggatatc tacttggtga                                              20

<210> SEQ ID NO 49
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium abscessus

<400> SEQUENCE: 49
taaacatagc ctcgctcgtt                                              20

<210> SEQ ID NO 50
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium abscessus

<400> SEQUENCE: 50
cgttttcgag tggggctggt                                              20

<210> SEQ ID NO 51
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium abscessus

<400> SEQUENCE: 51
gagtggggct ggttttttgca                                             20

<210> SEQ ID NO 52
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium abscessus

<400> SEQUENCE: 52
```

```
ctcgttttcg agtggggctg                                              20

<210> SEQ ID NO 53
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium vaccae

<400> SEQUENCE: 53
tcaggcccgc ccacatcgtg                                              20

<210> SEQ ID NO 54
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium vaccae

<400> SEQUENCE: 54 tggggttcg gtgatctgat                                               20

<210> SEQ ID NO 55
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium vaccae

<400> SEQUENCE: 55
cgattcgttg gatggccttt                                              20

<210> SEQ ID NO 56
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium vaccae

<400> SEQUENCE: 56
ggccgagccg gtagggaatg                                              20

<210> SEQ ID NO 57
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium vaccae

<400> SEQUENCE: 57
ccggcgaggg aaatcatcag                                              20

<210> SEQ ID NO 58
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium vaccae

<400> SEQUENCE: 58
```
acacactatt gggctttgag                                                  20

<210> SEQ ID NO 59
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium vaccae

<400> SEQUENCE: 59
acaacaagcc cgtgcccctt                                                  20

<210> SEQ ID NO 60
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium vaccae

<400> SEQUENCE: 60
ttttgggggt ggctctgcgt                                                  20

<210> SEQ ID NO 61
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium vaccae

<400> SEQUENCE: 61
tggcagggtc ggcgtgttgt                                                  20

<210> SEQ ID NO 62
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium vaccae

<400> SEQUENCE: 62
tgtttgattc gtggatagtg                                                  20

<210> SEQ ID NO 63
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium vaccae

<400> SEQUENCE: 63
gaatgcacag cgcttgtggt                                                  20

<210> SEQ ID NO 64
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium vaccae

<400> SEQUENCE: 64
gtgtgttcgg tgtaatgcaa                                                  20

<210> SEQ ID NO 65
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium flavescens

<400> SEQUENCE: 65
tttattgttc ccccgtcccc                                              20

<210> SEQ ID NO 66
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium flavescens

<400> SEQUENCE: 66
acgtgtgtgg gatcagtgcg                                              20

<210> SEQ ID NO 67
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium flavescens

<400> SEQUENCE: 67
gttgggagat cagtgccggg                                              20

<210> SEQ ID NO 68
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium flavescens

<400> SEQUENCE: 68
cctgtagtgg gtttccggtg                                              20

<210> SEQ ID NO 69
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium flavescens

<400> SEQUENCE: 69
cgtgagaagt ggtgtgggaa                                              20

<210> SEQ ID NO 70
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium flavescens

<400> SEQUENCE: 70
cactgctttg aggaatcatc                                              20

```
<210> SEQ ID NO 71
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium flavescens

<400> SEQUENCE: 71
ggcccgttgt ttccctggcc                                               20

<210> SEQ ID NO 72
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium flavescens

<400> SEQUENCE: 72
tgaacaggtg gctcccttttt                                              20

<210> SEQ ID NO 73
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium gordonae

<400> SEQUENCE: 73
cgacaacaag ctaagccaga                                               20

<210> SEQ ID NO 74
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium gordonae
<400> SEQUENCE: 74 tgttctttt gtgcaatttt                                                20

<210> SEQ ID NO 75
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium gordonae

<400> SEQUENCE: 75
gcatcaaaat gtatgcgttg                                               20

<210> SEQ ID NO 76
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium gordonae

<400> SEQUENCE: 76
aaaatgtatg cgttgtcgtt                                               20

<210> SEQ ID NO 77
```

```
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium gordonae

<400> SEQUENCE: 77
cggcaacgtg ttcttttttgt                                               20

<210> SEQ ID NO 78
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 78
ttgagttgtg gatagtggtt                                                20

<210> SEQ ID NO 79
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 79
gtcgagtgtt tagagagtaa                                                20

<210> SEQ ID NO 80
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 80
cgcactgggc gcattccgag                                                20

<210> SEQ ID NO 81
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 81 gtggggctg ggtgcacaac                                                 20

<210> SEQ ID NO 82
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 82
caacgttgaa aacaagatcg                                                20

<210> SEQ ID NO 83
<211> LENGTH: 20
```

<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 83
aattacgaac aacaacaagc                                              20

<210> SEQ ID NO 84
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 84
ttgcgagatc atcaactgcc                                              20

<210> SEQ ID NO 85
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 85
aggagtcctt ggggtttct                                               20

<210> SEQ ID NO 86
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 86
ggtggccggc ttttgtgctg                                              20

<210> SEQ ID NO 87
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 87
ggcacactgt tgggtcctga                                              20

<210> SEQ ID NO 88
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 88
ggcaacaggc ccgtttgtgc                                              20

<210> SEQ ID NO 89
<211> LENGTH: 20
<212> TYPE: DNA

```
<213> ORGANISM: Artificial Sequence
<220> FEATURE:
<223> OTHER INFORMATION: sequence of probe or primer for detecting
      Mycobacterium terrae

<400> SEQUENCE: 89
ccccgggtgg gggtgggtgt                                              20

<210> SEQ ID NO 90
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 90
gtgttgttgt cgcctcacac                                              20

<210> SEQ ID NO 91
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 91
taacaagcag atttttggtc                                              20

<210> SEQ ID NO 92
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 92
tggtctgttt gttttgcaat                                              20

<210> SEQ ID NO 93
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 93
ttttgtttct tggtttttgt                                              20

<210> SEQ ID NO 94
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 94
gtttgtaagt gtttaagggc                                              20

<210> SEQ ID NO 95
<211> LENGTH: 20
<212> TYPE: DNA
<213> ORGANISM: Artificial Sequence
```

-continued

```
<220> FEATURE:
<223> OTHER INFORMATION: sequence of probe or primer for detecting
      Mycobacterium terrae

<400> SEQUENCE: 95
gcatggtgga tgccttggca                                              20

<210> SEQ ID NO 96
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 96
cttttccccc cgtgcctcac                                              20

<210> SEQ ID NO 97
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 97
atgggtgagg gttttttgcgg                                             20

<210> SEQ ID NO 98
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 98
ttgggacagt gtttgccggt                                              20

<210> SEQ ID NO 99
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 99
gcctgtagtg ggtggccggt                                              20

<210> SEQ ID NO 100
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium terrae

<400> SEQUENCE: 100
ggtggccggt ggtgcagagg                                              20

<210> SEQ ID NO 101
<211> LENGTH: 20
<212> TYPE: DNA
<213> ORGANISM: Artificial Sequence
<220> FEATURE:
```

```
<223> OTHER INFORMATION: sequence of probe or primer for detecting
      Mycobacterium scrofluceum

<400> SEQUENCE: 101
cctgaggcaa cactcggctc                                                    20

<210> SEQ ID NO 102
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium scrofluceum

<400> SEQUENCE: 102
tcggctcgtt ctgagtggtg                                                    20

<210> SEQ ID NO 103
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium scrofluceum

<400> SEQUENCE: 103
taaacggatg cgtggccgaa                                                    20

<210> SEQ ID NO 104
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium scrofluceum

<400> SEQUENCE: 104
caacagcaaa tgattgccag                                                    20

<210> SEQ ID NO 105
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium scrofluceum

<400> SEQUENCE: 105
ccctccatct tggtggtggg                                                    20

<210> SEQ ID NO 106
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium scrofluceum

<400> SEQUENCE: 106
tgcgagcatc taaacggatg                                                    20

<210> SEQ ID NO 107
<211> LENGTH: 20
<212> TYPE: DNA
<213> ORGANISM: Artificial Sequence
<220> FEATURE:
<223> OTHER INFORMATION: sequence of probe or primer for detecting
```

Mycobacterium scrofluceum

<400> SEQUENCE: 107
gtggccgaac ggtggcgtgt                                              20

<210> SEQ ID NO 108
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium scrofluceum

<400> SEQUENCE: 108
tcgttgaaat gtgtaatttc                                              20

<210> SEQ ID NO 109
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium ka
<400> SEQUENCE: 109
gtggggtgca agccgtgagg                                              20

<210> SEQ ID NO 110
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium kansasii

<400> SEQUENCE: 110
gcgtgttctt ttgtgcaatt                                              20

<210> SEQ ID NO 111
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium kansasii

<400> SEQUENCE: 111
gcaactgtaa atgaatcacc                                              20

<210> SEQ ID NO 112
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium kansasii

<400> SEQUENCE: 112
ctggatgcgc tgccgttcgt                                              20

<210> SEQ ID NO 113
<211> LENGTH: 20
<212> TYPE: DNA
<213> ORGANISM: Artificial Sequence
<220> FEATURE:
<223> OTHER INFORMATION: sequence of probe or primer for detecting
       Mycobacterium szulgai

<400> SEQUENCE: 113
aacactcagg cttggccaga                                               20

<210> SEQ ID NO 114
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium szulgai

<400> SEQUENCE: 114
caattggatg cgctgccctc                                               20

<210> SEQ ID NO 115
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium szulgai

<400> SEQUENCE: 115
tcgtggtggc gtgttctttt                                               20

<210> SEQ ID NO 116
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium szulgai

<400> SEQUENCE: 116
gtgcaatttt aattctttgg                                               20

<210> SEQ ID NO 117
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium marinum
      and Mycobacterium ulcerans

<400> SEQUENCE: 117
aacaacaagc aagccagaca                                               20

<210> SEQ ID NO 118
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium marinum and Mycobacterium ulcerans

<400> SEQUENCE: 118
atctctgttg gtttcgggat                                               20

<210> SEQ ID NO 119
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium marinum and Mycobacterium ulcerans

<400> SEQUENCE: 119
ccttttggtg gcgtgttctg                                           20

<210> SEQ ID NO 120
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium gastri

<400> SEQUENCE: 120
aacagcaagc aagccagaca                                           20

<210> SEQ ID NO 121
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium gastri

<400> SEQUENCE: 121
ctcgtccaag agtgttgtcc                                           20

<210> SEQ ID NO 122
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium gastri

<400> SEQUENCE: 122
gcttgtcttg gactcgtcca                                           20

<210> SEQ ID NO 123
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium gastri

<400> SEQUENCE: 123
cagggtagcg tgttcttttg                                           20

<210> SEQ ID NO 124
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium xenopi

<400> SEQUENCE: 124
catctggcaa agactgtggt                                           20

<210> SEQ ID NO 125
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium xenopi

<400> SEQUENCE: 125
agggagcacc gtaaacgcat                                             20

<210> SEQ ID NO 126
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium xenopi

<400> SEQUENCE: 126
cccgcgtggg gtggggtgtg                                             20

<210> SEQ ID NO 127
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium xenopi

<400> SEQUENCE: 127
ggttcggcgt gttgtggcgt                                             20

<210> SEQ ID NO 128
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium xenopi

<400> SEQUENCE: 128
cgggccgagg tgttgggcag                                             20

<210> SEQ ID NO 129
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium xenopi

<400> SEQUENCE: 129
caggcagtaa ccgccggcac                                             20

<210> SEQ ID NO 130
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium xenopi

<400> SEQUENCE: 130
caggcagtaa ccgccggcac                                             20

<210> SEQ ID NO 131
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium xenopi

<400> SEQUENCE: 131
tccgcgtggt ggcggggtgt                                              20

<210> SEQ ID NO 132
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium xenopi

<400> SEQUENCE: 132
agactgtggt aagcggtttt                                              20

<210> SEQ ID NO 133
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium xenopi

<400> SEQUENCE: 133
tgttgagtgt tttctggtgt                                              20

<210> SEQ ID NO 134
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium genavense

<400> SEQUENCE: 134
cattgaatag tggttgcgag                                              20

<210> SEQ ID NO 135
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium genavense

<400> SEQUENCE: 135
aacaacaggc aatcgccgga                                              20

<210> SEQ ID NO 136
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium genavense

<400> SEQUENCE: 136
tcggccgact gaggtcgacg                                              20

<210> SEQ ID NO 137
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium genavense

<400> SEQUENCE: 137
gacgtggtgt ccctccatct                                              20

<210> SEQ ID NO 138
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium genavense

<400> SEQUENCE: 138
ttgagcattg aatagtggtt                                            20

<210> SEQ ID NO 139
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium genavense

<400> SEQUENCE: 139
gcgagcatct agacggatgc                                            20

<210> SEQ ID NO 140
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium genavense

<400> SEQUENCE: 140
gttccccagt ggtgcgcgtt                                            20

<210> SEQ ID NO 141
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium genavense

<400> SEQUENCE: 141
cgtcaaaaat gtgtaatttt                                            20

<210> SEQ ID NO 142
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium malmoense

<400> SEQUENCE: 142
agcatctaaa cggatgcgct                                            20

<210> SEQ ID NO 143
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium malmoense

<400> SEQUENCE: 143
tggtggggtg caagccgtga                                            20

<210> SEQ ID NO 144
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium malmoense

<400> SEQUENCE: 144
ccagtccgcg tggtgtcccc                                                    20

<210> SEQ ID NO 145
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium malmoense

<400> SEQUENCE: 145
tgcccgtaga cgcgtattcg                                                    20

<210> SEQ ID NO 146
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium malmoense

<400> SEQUENCE: 146
tttgtgtaat ttcttctttg                                                    20

<210> SEQ ID NO 147
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium simiae

<400> SEQUENCE: 147
acaacaacag gcaatcgcca                                                    20

<210> SEQ ID NO 148
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium simiae

<400> SEQUENCE: 148
actcggccga cttcggttga                                                    20

<210> SEQ ID NO 149
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium simiae

<400> SEQUENCE: 149
gagcatctaa atgaacgcgt                                                    20

```
<210> SEQ ID NO 150
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium simiae

<400> SEQUENCE: 150
tccaattggt ggggtgtgag                                              20

<210> SEQ ID NO 151
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium simiae

<400> SEQUENCE: 151
tgcacaacaa caggcaatcg                                              20

<210> SEQ ID NO 152
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium simiae

<400> SEQUENCE: 152
cgacttcggt tgaagtggtg                                              20

<210> SEQ ID NO 153
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium simiae

<400> SEQUENCE: 153
tacgtgttcg ttttgtgtaa                                              20

<210> SEQ ID NO 154
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium smegmatis

<400> SEQUENCE: 154
gacactctcc gttggggagg                                              20

<210> SEQ ID NO 155
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium smegmatis

<400> SEQUENCE: 155
gtgtgagccg tgaggagctg                                              20

<210> SEQ ID NO 156
```

```
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium smegmatis

<400> SEQUENCE: 156
gagcgctgta gtggcgccgg                                              20

<210> SEQ ID NO 157
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium smegmatis

<400> SEQUENCE: 157
cttggtgcac agcaaacgtt                                              20

<210> SEQ ID NO 158
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium smegmatis

<400> SEQUENCE: 158
gagatgcggt gtgggaaacg                                              20

<210> SEQ ID NO 159
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium smegmatis

<400> SEQUENCE: 159
ctgtttcgat ggactgccag                                              20

<210> SEQ ID NO 160
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium smegmatis

<400> SEQUENCE: 160
acacactatt gggccctgag                                              20

<210> SEQ ID NO 161
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium smegmatis

<400> SEQUENCE: 161
acaacaggcc cgcgttcccg                                              20

<210> SEQ ID NO 162
<211> LENGTH: 20
```

```
<212> TYPE: DNA
<213> ORGANISM: Artificial Sequence
<220> FEATURE:
<223> OTHER INFORMATION: sequence of probe or primer for detecting
      Mycobacterium smegmatis

<400> SEQUENCE: 162
tcccgttggg ggcgggggt                                                    20

<210> SEQ ID NO 163
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium smegmatis

<400> SEQUENCE: 163
gggtgtgttg ttgccctgct                                                   20

<210> SEQ ID NO 164
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium smegmatis

<400> SEQUENCE: 164
gctgtagtgg cgccggcttg                                                   20

<210> SEQ ID NO 165
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium smegmatis

<400> SEQUENCE: 165
aaacgctgtt tcgatggact                                                   20

<210> SEQ ID NO 166
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium shimoidei

<400> SEQUENCE: 166
aacaacaagc gagaagccga                                                   20

<210> SEQ ID NO 167
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium shimoidei

<400> SEQUENCE: 167
ggcttccgca gtgggcggaa                                                   20

<210> SEQ ID NO 168
<211> LENGTH: 20
<212> TYPE: DNA
```

-continued

<213> ORGANISM: Artificial Sequence
<220> FEATURE:
<223> OTHER INFORMATION: sequence of probe or primer for detecting
      Mycobacterium shimoidei

<400> SEQUENCE: 168
gggcgcgggc tgggtgcaca                                               20

<210> SEQ ID NO 169
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium shimoidei

<400> SEQUENCE: 169
gcgagaagcc gagcacactg                                               20

<210> SEQ ID NO 170
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium shimoidei

<400> SEQUENCE: 170
cccgggccct ttggggttgg                                               20

<210> SEQ ID NO 171
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium shimoidei

<400> SEQUENCE: 171
aagcaaaact tggttgtttt                                               20

<210> SEQ ID NO 172
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium shimoidei

<400> SEQUENCE: 172
gtttgtcgag ttgttttctt                                               20

<210> SEQ ID NO 173
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium habana

<400> SEQUENCE: 173
aacaacaggc aatcgccaga                                               20

<210> SEQ ID NO 174
<211> LENGTH: 20
<212> TYPE: DNA
<213> ORGANISM: Artificial Sequence

```
<220> FEATURE:
<223> OTHER INFORMATION: sequence of probe or primer for detecting
      Mycobacterium habana

<400> SEQUENCE: 174
aacactccaa ttgggtgggg                                                 20

<210> SEQ ID NO 175
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium habana

<400> SEQUENCE: 175
ggttctcgtc tgtagtggac                                                 20

<210> SEQ ID NO 176
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium habana

<400> SEQUENCE: 176
tgcacaacaa caggcaatcg                                                 20

<210> SEQ ID NO 177
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium habana

<400> SEQUENCE: 177
ggccgacttc ggttgaagtg                                                 20

<210> SEQ ID NO 178
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium habana

<400> SEQUENCE: 178
ggggtgtggt gtttgagtat                                                 20

<210> SEQ ID NO 179
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium habana

<400> SEQUENCE: 179
gagcatctaa atgaacgcgt                                                 20

<210> SEQ ID NO 180
<211> LENGTH: 20
<212> TYPE: DNA
<213> ORGANISM: Artificial Sequence
<220> FEATURE:
```

<223> OTHER INFORMATION: sequence of probe or primer for detecting
      Mycobacterium habana

<400> SEQUENCE: 180
tacgtgttcg ttttgtgtaa 20

<210> SEQ ID NO 181
<211> LENGTH: 20
<212> TYPE: DNA
<213> ORGANISM: Artificial Sequence
<220> FEATURE:
<223> OTHER INFORMATION: sequence of probe or primer for detecting
Mycobacterium farcinogen

<400> SEQUENCE: 181
gttggtgatg gactgccaga 20

<210> SEQ ID NO 182
<211> LENGTH: 20
<212> TYPE: DNA
<213> ORGANISM: Artificial Sequence
<220> FEATURE:
<223> OTHER INFORMATION: sequence of probe or primer for detecting
Mycobacterium farcinogen

<400> SEQUENCE: 182
cgcgggaaag cgttggtgat 20

<210> SEQ ID NO 183
<211> LENGTH: 20
<212> TYPE: DNA
<213> ORGANISM: Artificial Sequence
<220> FEATURE:
<223> OTHER INFORMATION: sequence of probe or primer for detecting
Mycobacterium farcinogen

<400> SEQUENCE: 183
cgatgtcgtg ggcagtagtg 20

<210> SEQ ID NO 184
<211> LENGTH: 20
<212> TYPE: DNA
<213> ORGANISM: Artificial Sequence
<220> FEATURE:
<223> OTHER INFORMATION: sequence of probe or primer for detecting
Mycobacterium farcinogen

<400> SEQUENCE: 184
ggatatttca gccagcatct 20

<210> SEQ ID NO 185
<211> LENGTH: 20
<212> TYPE: DNA
<213> ORGANISM: Artificial Sequence
<220> FEATURE:
<223> OTHER INFORMATION: sequence of probe or primer for detecting
Mycobacterium farcinogen

<400> SEQUENCE: 185
tgtctggtgg gtgcaaatga 20

<210> SEQ ID NO 186
<211> LENGTH: 20
<212> TYPE: DNA
<213> ORGANISM: Artificial Sequence
<220> FEATURE:
<223> OTHER INFORMATION: sequence of probe or primer for detecting

```
      Mycobacterium farcinogen

<400> SEQUENCE: 186
cggcgcggga aagcgttggt                                              20

<210> SEQ ID NO 187
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium farcinogen

<400> SEQUENCE: 187
gggaaagcgt tggtgatgga                                              20

<210> SEQ ID NO 188
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium farcinogen

<400> SEQUENCE: 188
tctagcacgc agagtgtggc                                              20

<210> SEQ ID NO 189
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium farcinogen

<400> SEQUENCE: 189
tgggggcctt cgggtttctt                                              20

<210> SEQ ID NO 190
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium asiaticum

<400> SEQUENCE: 190
catcccaatt ggtgggatgc                                              20

<210> SEQ ID NO 191
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium asiaticum

<400> SEQUENCE: 191
cacaacaaca agcaagccag                                              20

<210> SEQ ID NO 192
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium asiaticum
```

<400> SEQUENCE: 192
cactcgggcg ctagcacgaa                                               20

<210> SEQ ID NO 193
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium asiaticum

<400> SEQUENCE: 193
aactgatcgc gtcgccgttc                                               20

<210> SEQ ID NO 194
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium porcinum

<400> SEQUENCE: 194
cagtagtgcg gttgggatat                                               20

<210> SEQ ID NO 195
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium porcinum

<400> SEQUENCE: 195
ttcgattccc ccgccgtccg                                               20

<210> SEQ ID NO 196
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium porcinum

<400> SEQUENCE: 196
cagccaggac ctgtagtggg                                               20

<210> SEQ ID NO 197
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium porcinum

<400> SEQUENCE: 197
tggtgggtgc aaatgacaaa                                               20

<210> SEQ ID NO 198
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium porcinum -continued

<400> SEQUENCE: 198
gagccggcgc gggaaagcgt                                           20

<210> SEQ ID NO 199
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium porcinum

<400> SEQUENCE: 199
gtgatggaac tgctgaacac                                           20

<210> SEQ ID NO 200
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium porcinum

<400> SEQUENCE: 200
ggctttgaga caacaggccc                                           20

<210> SEQ ID NO 201
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium porcinum

<400> SEQUENCE: 201
cggggggtgg cattccgttg                                           20

<210> SEQ ID NO 202
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium porcinum

<400> SEQUENCE: 202
cggcgtgttg ttgctccgct                                           20

<210> SEQ ID NO 203
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium porcinum

<400> SEQUENCE: 203
tagtggttgc gagcatctag                                           20

<210> SEQ ID NO 204
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium porcinum

<400> SEQUENCE: 204
agtgtggctg ggggccttcg                                                    20

<210> SEQ ID NO 205
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium porcinum

<400> SEQUENCE: 205
ggtcttgttg tgtgttgatg                                                    20

<210> SEQ ID NO 206
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium acapulcensis

<400> SEQUENCE: 206
tgccagcacc tgtagtgggt                                                    20

<210> SEQ ID NO 207
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium acapulcensis

<400> SEQUENCE: 207
gatcgtctgg tggggaaagc                                                    20

<210> SEQ ID NO 208
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium acapulcensis

<400> SEQUENCE: 208
cgggcgtgaa agattgccag                                                    20

<210> SEQ ID NO 209
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium acapulcensis

<400> SEQUENCE: 209
agcccgtcgc ctctttgtcc                                                    20

<210> SEQ ID NO 210
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium acapulcensis

<400> SEQUENCE: 210

-continued cgagtgtggg atatcggaga 20

<210> SEQ ID NO 211
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium acapulcensis

<400> SEQUENCE: 211
ggagcaccac gagacctgtt 20

<210> SEQ ID NO 212
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium acapulcensis

<400> SEQUENCE: 212
cgcccacatc gtgtgggagt 20

<210> SEQ ID NO 213
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium acapulcensis

<400> SEQUENCE: 213
tcggtgactc aggcgattcg 20

<210> SEQ ID NO 214
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium acapulcensis

<400> SEQUENCE: 214
gggtgtggtg tttgatttgt 20

<210> SEQ ID NO 215
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium acapulcensis

<400> SEQUENCE: 215
cgagcatctg aacgcagaga 20

<210> SEQ ID NO 216
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium diernhoferi

<400> SEQUENCE: 216
acctgttgcc cgcccacatc 20

<210> SEQ ID NO 217
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium diernhoferi

<400> SEQUENCE: 217
gtgtgggagt tcggtgactc                                              20

<210> SEQ ID NO 218
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium diernhoferi

<400> SEQUENCE: 218
ttcgttggat ggcctcacac                                              20

<210> SEQ ID NO 219
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium diernhoferi

<400> SEQUENCE: 219
tgcacaacaa actttgagaa                                              20

<210> SEQ ID NO 220
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium diernhoferi

<400> SEQUENCE: 220
acaggccctg cggtgccgga                                              20

<210> SEQ ID NO 221
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium diernhoferi

<400> SEQUENCE: 221
tcgttggagt cctggttgcc                                              20

<210> SEQ ID NO 222
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium diernhoferi

<400> SEQUENCE: 222
ggccgcgagt cccggaagcg                                              20

<210> SEQ ID NO 223
<211> LENGTH: 20
<212> TYPE: DNA
<213> ORGANISM: Artificial Sequence
<220> FEATURE:
<223> OTHER INFORMATION: sequence of probe or primer for detecting
     Mycobacterium diernhoferi

<400> SEQUENCE: 223
gtctgttgtt gctccatctt                                                   20

<210> SEQ ID NO 224
<211> LENGTH: 20
<212> TYPE: DNA
<213> ORGANISM: Artificial Sequence
<220> FEATURE:
<223> OTHER INFORMATION: sequence of probe or primer for detecting
     Mycobacterium diernhoferi

<400> SEQUENCE: 224
ggtgtggtgt ttgatttgtg                                                   20

<210> SEQ ID NO 225
<211> LENGTH: 20
<212> TYPE: DNA
<213> ORGANISM: Artificial Sequence
<220> FEATURE:
<223> OTHER INFORMATION: sequence of probe or primer for detecting
     Mycobacterium diernhoferi

<400> SEQUENCE: 225
atagtggttg cgagcatcta                                                   20

<210> SEQ ID NO 226
<211> LENGTH: 20
<212> TYPE: DNA
<213> ORGANISM: Artificial Sequence
<220> FEATURE:
<223> OTHER INFORMATION: sequence of probe or primer for detecting
     Mycobacterium diernhoferi

<400> SEQUENCE: 226
acgcaagagg agtctgggtt                                                   20

<210> SEQ ID NO 227
<211> LENGTH: 20
<212> TYPE: DNA
<213> ORGANISM: Artificial Sequence
<220> FEATURE:
<223> OTHER INFORMATION: sequence of probe or primer for detecting
     Mycobacterium diernhoferi

<400> SEQUENCE: 227
ttgttgtgtg tgtttgatgt                                                   20

<210> SEQ ID NO 228
<211> LENGTH: 20
<212> TYPE: DNA
<213> ORGANISM: Artificial Sequence
<220> FEATURE:
<223> OTHER INFORMATION: sequence of probe or primer for detecting
     Mycobacterium paratuberculosis

<400> SEQUENCE: 228
gagcaccacg aaaagcaccc                                                   20

<210> SEQ ID NO 229
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium paratuberculosis

<400> SEQUENCE: 229
ctggtggggt gcgagccgtg                                                      20

<210> SEQ ID NO 230
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium paratuberculosis

<400> SEQUENCE: 230
gcgagccgtg agggttccc                                                       20

<210> SEQ ID NO 231
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium paratuberculosis

<400> SEQUENCE: 231
aggggttccc gtctgtagtg                                                      20

<210> SEQ ID NO 232
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium paratuberculosis

<400> SEQUENCE: 232 acggggccg ggtgcgcaac                                                       20

<210> SEQ ID NO 233
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium paratuberculosis

<400> SEQUENCE: 233
caaatgattg ccagacacac                                                      20

<210> SEQ ID NO 234
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium paratuberculosis

<400> SEQUENCE: 234
tattgggcct gagacaacac                                                      20

<210> SEQ ID NO 235

```
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium paratuberculosis

<400> SEQUENCE: 235
cggtccgtcc gtgtggagtc                                                    20

<210> SEQ ID NO 236
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium paratuberculosis

<400> SEQUENCE: 236
tccatcttgg tggtggggtg                                                    20

<210> SEQ ID NO 237
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium paratuberculosis

<400> SEQUENCE: 237
ggtgtttgag tattggatag                                                    20

<210> SEQ ID NO 238
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium paratuberculosis

<400> SEQUENCE: 238
tggttgcgag catctagatg                                                    20

<210> SEQ ID NO 239
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium paratuberculosis

<400> SEQUENCE: 239
gcgcatggtc tccgtggccg                                                    20

<210> SEQ ID NO 240
<211> LENGTH: 20
<212> TYPE: DNA
<213> ORGANISM: Artificial Sequence
<220> FEATURE:
<223> OTHER INFORMATION: sequence of probe or primer for detecting
      Mycobacterium paratuberculosis

<400> SEQUENCE: 240
gttcatcgaa atgtgtaatt                                                    20

<210> SEQ ID NO 241
<211> LENGTH: 20
```

```
<212> TYPE: DNA
<213> ORGANISM: Artificial Sequence
<220> FEATURE:
<223> OTHER INFORMATION: sequence of probe or primer for detecting
      Mycobacteria sp.

<400> SEQUENCE: 241
aaaagctgtt gtttgacggt                                              20

<210> SEQ ID NO 242
<211> LENGTH: 25
<212> TYPE: DNA
<213> ORGANISM: Artificial Sequence
<220> FEATURE:
<223> OTHER INFORMATION: sequence of primer for amplifying Mycobacteria
      ITS selected from the sequence of 16S rRNA in Mycobacteria

<400> SEQUENCE: 242
tggatccgac gaagtcgtaa caagg                                        25

<210> SEQ ID NO 243
<211> LENGTH: 25
<212> TYPE: DNA
<213> ORGANISM: Artificial Sequence
<220> FEATURE:
<223> OTHER INFORMATION: sequence of primer for amplifying Mycobacteria
      ITS selected from the sequence of 23S rRNA in Mycobacteria

<400> SEQUENCE: 243
tggatcctgc caaggcatcc accat                                        25
```